United States Patent
Angel et al.

(10) Patent No.: US 9,101,450 B2
(45) Date of Patent: Aug. 11, 2015

(54) MULTI-LUMEN CENTRAL ACCESS VENA CAVA FILTER APPARATUS AND METHOD OF USING SAME

(71) Applicant: BiO2 Medical, Inc., San Antonio, TX (US)

(72) Inventors: Luis F. Angel, San Antonio, TX (US); Jeffrey N. Steinmetz, Arvada, CO (US)

(73) Assignee: BIO2 MEDICAL, INC., Golden, CO (US)

(*) Notice: Subject to any disclaimer, the term of this patent is extended or adjusted under 35 U.S.C. 154(b) by 0 days.

(21) Appl. No.: 13/722,221

(22) Filed: Dec. 20, 2012

(65) Prior Publication Data

US 2013/0197565 A1    Aug. 1, 2013

Related U.S. Application Data

(63) Continuation of application No. 12/684,839, filed on Jan. 8, 2010, now Pat. No. 8,613,753, which is a continuation-in-part of application No. 11/849,225, filed on Aug. 31, 2007, now Pat. No. 8,668,712.

(51) Int. Cl.
*A61M 29/00* (2006.01)
*A61F 2/01* (2006.01)
*A61M 25/00* (2006.01)

(52) U.S. Cl.
CPC . *A61F 2/01* (2013.01); *A61F 2/013* (2013.01); *A61M 25/0029* (2013.01); *A61F 2002/016* (2013.01); *A61F 2002/018* (2013.01); *A61F 2230/008* (2013.01); *A61F 2230/0093* (2013.01);

(Continued)

(58) Field of Classification Search
CPC ..... A61F 2/01; A61F 2002/011; A61F 2/013; A61F 2002/016
USPC ........................................................ 606/200
See application file for complete search history.

(56) References Cited

U.S. PATENT DOCUMENTS

| 3,671,979 A | 6/1972 | Moulopoulos ........................ 3/1 |
| 4,901,731 A | 2/1990 | Millar ........................... 128/675 |

(Continued)

FOREIGN PATENT DOCUMENTS

| WO | 96/30073 | 10/1996 | ............ A61M 29/00 |
| WO | 97/17100 | 5/1997 | ............ A61M 29/00 |

(Continued)

OTHER PUBLICATIONS

Decousus, Herve, et al., "A Clinical Trial of Vena Caval Filters in the Prevention of Pulmonary Embolism in Patients with Proximal Deep-Vein Thrombisis", *The New England Journal of Medicine*, vol. 338, No. 7, pp. 409-415 (Feb. 12, 1998).

(Continued)

*Primary Examiner* — Victor Nguyen
*Assistant Examiner* — Kevin Everage
(74) *Attorney, Agent, or Firm* — David G. Rosenbaum; J. Peter Paredes; Rosenbaum IP, P.C.

(57) ABSTRACT

A combined multi-lumen central access catheter and an embolic filter including ports proximal and distal the filter for fluid infusion and/or pressure sensing and infusion ports in the catheter to permit infusion of bioactive agents, flushing agents and/or contrast agents. The embolic filter may be removably coupled to the multi-lumen catheter for temporary placement and retrieval under recommended indications.

15 Claims, 14 Drawing Sheets

(52) U.S. Cl.
CPC .............. *A61M 2025/0002* (2013.01); *A61M 2025/0003* (2013.01); *A61M 2025/004* (2013.01); *A61M 2025/0036* (2013.01); *A61M 2205/3523* (2013.01)

(56) References Cited

U.S. PATENT DOCUMENTS

| | | | |
|---|---|---|---|
| 4,921,479 A | 5/1990 | Grayzel | 604/53 |
| 4,969,891 A | 11/1990 | Gerwertz | 606/200 |
| 5,046,503 A | 9/1991 | Schneiderman | 128/692 |
| 5,053,008 A | 10/1991 | Bajaj | 604/104 |
| 5,112,347 A | 5/1992 | Taheri | 606/200 |
| 5,163,928 A | 11/1992 | Hobbs et al. | 604/281 |
| 5,201,757 A | 4/1993 | Heyn et al. | 606/200 |
| 5,549,626 A | 8/1996 | Miller et al. | 606/200 |
| 5,569,215 A | 10/1996 | Crocker | 604/264 |
| 5,624,396 A | 4/1997 | McNamara et al. | 604/93 |
| 5,707,389 A | 1/1998 | Louw et al. | 606/200 |
| 5,715,829 A | 2/1998 | Arand et al. | 128/673 |
| 5,766,151 A | 6/1998 | Valley et al. | 604/96 |
| 5,769,816 A | 6/1998 | Barbut et al. | 604/96 |
| 5,791,341 A | 8/1998 | Bullard | 128/207.15 |
| 5,795,322 A | 8/1998 | Boudewijn | 604/2 |
| 5,795,325 A | 8/1998 | Valley et al. | 604/53 |
| 5,797,920 A | 8/1998 | Kim | 606/108 |
| 5,814,064 A | 9/1998 | Daniel et al. | 606/200 |
| 5,833,650 A | 11/1998 | Imran | 604/53 |
| 5,848,964 A | 12/1998 | Samuels | 600/200 |
| 5,879,499 A | 3/1999 | Corvi | 156/175 |
| 5,893,868 A | 4/1999 | Hanson et al. | 606/198 |
| 5,925,016 A | 7/1999 | Chornenky et al. | 604/96 |
| 5,947,994 A | 9/1999 | Louw et al. | 606/200 |
| 5,947,995 A | 9/1999 | Samuels | 606/200 |
| 5,954,742 A | 9/1999 | Osypka | 606/198 |
| 5,976,172 A | 11/1999 | Homsma et al. | 606/200 |
| 5,980,478 A | 11/1999 | Gorsuch et al. | 604/4 |
| 5,980,555 A | 11/1999 | Barbut et al. | 600/200 |
| 5,989,281 A | 11/1999 | Barbut et al. | 606/200 |
| 6,007,544 A | 12/1999 | Kim | 606/108 |
| 6,036,654 A | 3/2000 | Quinn et al. | 600/526 |
| 6,051,014 A | 4/2000 | Jang | 606/200 |
| 6,086,605 A | 7/2000 | Barbut et al. | 606/200 |
| 6,090,097 A | 7/2000 | Barbut et al. | 604/511 |
| 6,117,154 A | 9/2000 | Barbut et al. | 606/181 |
| 6,135,991 A | 10/2000 | Muni et al. | 604/509 |
| 6,136,016 A | 10/2000 | Barbut et al. | 606/200 |
| 6,152,909 A | 11/2000 | Bagaoisan et al. | 604/523 |
| 6,165,179 A | 12/2000 | Cathcart et al. | 606/108 |
| 6,171,328 B1 | 1/2001 | Addis | 606/200 |
| 6,178,968 B1 | 1/2001 | Louw et al. | 128/898 |
| 6,179,813 B1 | 1/2001 | Ballow et al. | 604/164 |
| 6,224,627 B1 | 5/2001 | Armstrong et al. | 623/1.23 |
| 6,231,544 B1 | 5/2001 | Tsugita et al. | 604/104 |
| 6,235,045 B1 | 5/2001 | Barbut et al. | 606/200 |
| 6,251,093 B1 | 6/2001 | Valley et al. | 604/96 |
| 6,270,477 B1 | 8/2001 | Bagaoisan et al. | 604/96.01 |
| 6,277,138 B1 | 8/2001 | Levinson et al. | 606/200 |
| 6,287,321 B1 | 9/2001 | Jang | 606/200 |
| 6,315,792 B1 | 11/2001 | Armstrong et al. | 623/1.13 |
| 6,336,934 B1 | 1/2002 | Gilson et al. | 606/200 |
| 6,344,049 B1 | 2/2002 | Levinson et al. | 606/200 |
| 6,344,053 B1 | 2/2002 | Boneau | 623/1.11 |
| 6,379,373 B1 | 4/2002 | Sawhney et al. | 606/193 |
| 6,383,196 B1 | 5/2002 | Leslie et al. | 606/114 |
| 6,423,086 B1 | 7/2002 | Barbut et al. | 606/200 |
| 6,432,122 B1 | 8/2002 | Gilson et al. | 606/200 |
| 6,443,971 B1 | 9/2002 | Boylan et al. | 606/200 |
| 6,454,741 B1 | 9/2002 | Muni et al. | 604/96.01 |
| 6,468,291 B2 | 10/2002 | Bates et al. | 606/200 |
| 6,482,171 B1 | 11/2002 | Corvi et al. | 604/96.01 |
| 6,511,503 B1 | 1/2003 | Burkett et al. | 623/1.11 |
| 6,537,294 B1 | 3/2003 | Boyle et al. | 606/200 |
| 6,537,296 B2 * | 3/2003 | Levinson et al. | 606/200 |
| 6,544,279 B1 | 4/2003 | Hopkins et al. | 606/200 |
| 6,547,788 B1 | 4/2003 | Maguire et al. | 604/41 |
| 6,561,996 B1 | 5/2003 | Gorsuch | 604/6.09 |
| 6,569,148 B2 | 5/2003 | Bagaoisan et al. | 604/509 |
| 6,585,639 B1 | 7/2003 | Kotmel et al. | 600/116 |
| 6,589,264 B1 | 7/2003 | Barbut et al. | 606/200 |
| 6,592,546 B1 | 7/2003 | Barbut et al. | 604/96.01 |
| 6,596,011 B2 | 7/2003 | Johnson et al. | 606/200 |
| 6,616,680 B1 | 9/2003 | Theilen | 606/200 |
| 6,623,507 B2 | 9/2003 | Saleh | 606/200 |
| 6,635,070 B2 | 10/2003 | Leeflang et al. | 606/200 |
| 6,669,708 B1 | 12/2003 | Nissenbaum et al. | 606/153 |
| 6,685,722 B2 | 2/2004 | Rosenbluth et al. | 606/200 |
| 6,689,148 B2 | 2/2004 | Sawhney et al. | 606/193 |
| 6,692,512 B2 | 2/2004 | Jang | 606/200 |
| 6,726,651 B1 | 4/2004 | Robinson et al. | 604/101.01 |
| 6,726,702 B2 | 4/2004 | Khosravi | 606/200 |
| 6,749,619 B2 | 6/2004 | Ouriel et al. | 606/200 |
| 6,755,813 B2 | 6/2004 | Ouriel et al. | 604/537 |
| 6,780,193 B2 | 8/2004 | Leslie et al. | 606/114 |
| 6,805,692 B2 | 10/2004 | Muni et al. | 604/509 |
| 6,869,431 B2 | 3/2005 | Maguire et al. | 604/41 |
| 6,885,115 B2 | 4/2005 | Hatori et al. | 307/80 |
| 6,887,257 B2 | 5/2005 | Salahieh et al. | 606/200 |
| 6,913,600 B2 | 7/2005 | Valley et al. | 604/509 |
| 6,986,778 B2 | 1/2006 | Zadno-Azizi | 606/200 |
| 6,997,938 B2 | 2/2006 | Wang et al. | 606/200 |
| 7,011,672 B2 | 3/2006 | Barbut et al. | 606/200 |
| 7,060,082 B2 | 6/2006 | Goll et al. | 606/200 |
| 7,108,708 B2 | 9/2006 | Cheng et al. | 606/200 |
| 7,125,414 B2 | 10/2006 | Blackledge et al. | 606/200 |
| 7,144,408 B2 | 12/2006 | Keegan et al. | 606/200 |
| 7,150,737 B2 | 12/2006 | Purdy et al. | 604/506 |
| 7,153,320 B2 | 12/2006 | Euteneuer et al. | 606/200 |
| 7,163,520 B2 | 1/2007 | Bernard et al. | 604/6.9 |
| 7,166,570 B1 | 1/2007 | Hunter et al. | 514/2 |
| 7,220,270 B2 | 5/2007 | Sawhney et al. | 606/193 |
| 7,261,727 B2 | 8/2007 | Thielen | 606/200 |
| 7,399,308 B2 | 7/2008 | Borillo et al. | 606/200 |
| 2001/0001812 A1 | 5/2001 | Valley et al. | 604/96.01 |
| 2001/0031981 A1 | 10/2001 | Evans et al. | 606/200 |
| 2001/0044634 A1 | 11/2001 | Don Michael et al. | 606/200 |
| 2002/0062134 A1 | 5/2002 | Barbut et al. | 606/200 |
| 2002/0072730 A1 | 6/2002 | McGill et al. | 604/525 |
| 2002/0082525 A1 | 6/2002 | Oslund et al. | 600/585 |
| 2002/0082636 A1 | 6/2002 | Sawhney et al. | 606/193 |
| 2002/0091407 A1 | 7/2002 | Zadno-Azizi et al. | 606/200 |
| 2002/0107479 A1 | 8/2002 | Bates et al. | 604/96.01 |
| 2002/0107506 A1 | 8/2002 | McGuckin, Jr. et al. | 604/523 |
| 2002/0165575 A1 | 11/2002 | Saleh | 606/200 |
| 2002/0188313 A1 | 12/2002 | Johnson et al. | 606/200 |
| 2003/0009146 A1 | 1/2003 | Muni et al. | 604/500 |
| 2003/0032941 A1 | 2/2003 | Boyle et al. | 604/533 |
| 2003/0050600 A1 | 3/2003 | Ressemann et al. | 604/101.01 |
| 2003/0093110 A1 | 5/2003 | Vale | 606/200 |
| 2003/0097082 A1 | 5/2003 | Purdy et al. | 606/594 |
| 2003/0097094 A1 | 5/2003 | Ouriel et al. | 604/93.01 |
| 2003/0176889 A1 | 9/2003 | Boyle et al. | 606/200 |
| 2003/0187495 A1 | 10/2003 | Cully et al. | 623/1.15 |
| 2003/0203031 A1 | 10/2003 | Shah | 424/485 |
| 2003/0208222 A1 | 11/2003 | Zadno-Azizi | 606/194 |
| 2003/0212434 A1 | 11/2003 | Thielen | 606/200 |
| 2003/0233117 A1 | 12/2003 | Adams et al. | 606/200 |
| 2004/0006367 A1 | 1/2004 | Johnson et al. | 606/200 |
| 2004/0006368 A1 | 1/2004 | Mazzocchi et al. | 606/200 |
| 2004/0011740 A1 | 1/2004 | Bernard et al. | 210/646 |
| 2004/0044302 A1 | 3/2004 | Bernard et al. | 604/6.09 |
| 2004/0102806 A1* | 5/2004 | Broome et al. | 606/200 |
| 2004/0127934 A1 | 7/2004 | Brady et al. | 606/200 |
| 2004/0153112 A1 | 8/2004 | Nissenbaum et al. | 606/185 |
| 2004/0158276 A1 | 8/2004 | Barbut et al. | 606/200 |
| 2004/0162576 A1* | 8/2004 | Barbut et al. | 606/200 |
| 2004/0199177 A1 | 10/2004 | Kim | 606/108 |
| 2004/0220612 A1 | 11/2004 | Swainston et al. | 606/200 |
| 2004/0236170 A1 | 11/2004 | Kim | 600/16 |
| 2004/0254528 A1 | 12/2004 | Adams et al. | 604/96.01 |
| 2005/0021075 A1 | 1/2005 | Bonnette et al. | 606/200 |
| 2005/0027236 A1 | 2/2005 | Douk et al. | 604/40 |
| 2005/0038503 A1 | 2/2005 | Greenhalgh et al. | 623/1.42 |
| 2005/0080445 A1 | 4/2005 | Sawhney et al. | 606/193 |
| 2005/0085769 A1 | 4/2005 | MacMahon et al. | 604/96.01 |

(56) References Cited

U.S. PATENT DOCUMENTS

| | | | |
|---|---|---|---|
| 2005/0085841 A1 | 4/2005 | Eversull et al. | 606/190 |
| 2005/0107817 A1 | 5/2005 | White et al. | 606/191 |
| 2005/0113862 A1 | 5/2005 | Besselink et al. | 606/200 |
| 2005/0133046 A1 | 6/2005 | Becker et al. | 128/898 |
| 2005/0142163 A1 | 6/2005 | Hunter et al. | 424/423 |
| 2005/0145258 A1 | 7/2005 | Dong | 128/898 |
| 2005/0147562 A1 | 7/2005 | Hunter et al. | 424/9.5 |
| 2005/0147599 A1 | 7/2005 | Hunter et al. | 424/94.63 |
| 2005/0147643 A1 | 7/2005 | Hunter et al. | 424/423 |
| 2005/0148512 A1 | 7/2005 | Hunter et al. | 514/12 |
| 2005/0148997 A1 | 7/2005 | Valley et al. | 604/509 |
| 2005/0158274 A1 | 7/2005 | Hunter et al. | 424/78.38 |
| 2005/0169958 A1 | 8/2005 | Hunter et al. | 424/423 |
| 2005/0169959 A1 | 8/2005 | Hunter et al. | 424/423 |
| 2005/0175657 A1 | 8/2005 | Hunter et al. | 424/422 |
| 2005/0177186 A1* | 8/2005 | Cully et al. | 606/200 |
| 2005/0186247 A1 | 8/2005 | Hunter et al. | 424/423 |
| 2005/0191248 A1 | 9/2005 | Hunter et al. | 424/50 |
| 2005/0192620 A1 | 9/2005 | Cully et al. | 606/200 |
| 2005/0197624 A1 | 9/2005 | Goodson, IV et al. | 604/96.01 |
| 2005/0205097 A1 | 9/2005 | Kyle, Jr. | 128/207.14 |
| 2005/0245962 A1 | 11/2005 | Adams et al. | 606/194 |
| 2005/0261733 A1 | 11/2005 | Cheng et al. | 606/200 |
| 2005/0267408 A1 | 12/2005 | Grandt et al. | 604/103.04 |
| 2005/0267442 A1 | 12/2005 | Von Oepen | 604/509 |
| 2005/0277976 A1 | 12/2005 | Galdonik et al. | 606/200 |
| 2005/0283182 A1 | 12/2005 | Pierce et al. | 606/200 |
| 2005/0288704 A1 | 12/2005 | Cartier et al. | 606/200 |
| 2006/0047300 A1 | 3/2006 | Eidenschink | |
| 2006/0135961 A1 | 6/2006 | Rosenman et al. | 606/108 |
| 2006/0184048 A1* | 8/2006 | Saadat | 600/478 |
| 2006/0189921 A1 | 8/2006 | Galdonik et al. | 604/27 |
| 2006/0190025 A1 | 8/2006 | Lehe et al. | 606/200 |
| 2006/0200191 A1 | 9/2006 | Zadno-Azizi | 606/200 |
| 2006/0229657 A1 | 10/2006 | Wasicek et al. | 606/200 |
| 2006/0240063 A9 | 10/2006 | Hunter et al. | 424/423 |
| 2006/0240064 A9 | 10/2006 | Hunter et al. | 424/423 |
| 2006/0241675 A1 | 10/2006 | Johnson et al. | 606/200 |
| 2006/0241676 A1 | 10/2006 | Johnson et al. | 606/200 |
| 2006/0241677 A1 | 10/2006 | Johnson et al. | 606/200 |
| 2006/0241678 A1 | 10/2006 | Johnson et al. | 606/200 |
| 2006/0241679 A1 | 10/2006 | Johnson et al. | 606/200 |
| 2006/0241680 A1 | 10/2006 | Johnson et al. | 606/200 |
| 2006/0248871 A1 | 11/2006 | Johnson et al. | 57/58.83 |
| 2006/0271098 A1 | 11/2006 | Peacock, III | 606/200 |
| 2007/0006441 A1 | 1/2007 | McNiven et al. | 29/508 |
| 2007/0016132 A1 | 1/2007 | Oepen et al. | 604/96.01 |
| 2007/0016165 A1 | 1/2007 | Von Oepen et al. | 604/525 |
| 2007/0021771 A1 | 1/2007 | Oepen et al. | 606/194 |
| 2007/0055365 A1 | 3/2007 | Greenberg et al. | 623/1.44 |
| 2007/0060942 A2 | 3/2007 | Zadno-Azizi | 606/194 |
| 2007/0065484 A1 | 3/2007 | Chudzik et al. | 424/426 |
| 2007/0083188 A1 | 4/2007 | Grandt et al. | 604/524 |
| 2007/0123838 A1 | 5/2007 | Bernard et al. | 604/500 |
| 2007/0129752 A1 | 6/2007 | Webler et al. | 606/200 |
| 2007/0129753 A1 | 6/2007 | Quinn et al. | 606/200 |
| 2007/0191717 A1 | 8/2007 | Rosen et al. | 600/485 |
| 2007/0204455 A1 | 9/2007 | Knott et al. | 29/508 |
| 2007/0208374 A1 | 9/2007 | Boyle et al. | 606/200 |
| 2007/0244503 A1 | 10/2007 | Casey et al. | 606/200 |
| 2007/0293930 A1 | 12/2007 | Wang et al. | 623/1.11 |
| 2008/0027481 A1 | 1/2008 | Gilson et al. | 606/200 |
| 2008/0051671 A1 | 2/2008 | Broome et al. | 600/504 |
| 2008/0262532 A1 | 10/2008 | Martin | |

FOREIGN PATENT DOCUMENTS

| | | | |
|---|---|---|---|
| WO | 97/42879 | 11/1997 | A61B 17/00 |
| WO | 98/46297 | 10/1998 | A61M 29/00 |
| WO | 99/65420 | 12/1999 | A61F 2/06 |
| WO | 00/09190 | 2/2000 | A61M 25/00 |
| WO | 01/13983 | 3/2001 | A61M 25/00 |
| WO | 01/37921 | 5/2001 | A61M 29/00 |
| WO | 01/65936 | 9/2001 | C12N 11/04 |
| WO | 02/30271 | 4/2002 | |
| WO | 02/39878 | 5/2002 | |
| WO | 02/40090 | 5/2002 | A61M 29/00 |
| WO | 03/015859 | 2/2003 | A61M 25/06 |
| WO | 03/084437 | 10/2003 | A61F 2/03 |
| WO | 2004/014240 | 2/2004 | A61B 17/12 |
| WO | 2004/034884 | 4/2004 | |
| WO | 2004/054650 | 7/2004 | A61M 25/00 |
| WO | 2004/060465 | 7/2004 | A61M 25/06 |
| WO | 2004/098674 | 11/2004 | |
| WO | 2005/011786 | 2/2005 | A61M 25/00 |
| WO | 2005/023358 | 3/2005 | A61M 25/00 |
| WO | 2005/046746 | 5/2005 | A61B 17/11 |
| WO | 2005/058384 | 6/2005 | A61L 29/00 |
| WO | 2005/065079 | 7/2005 | A61F 2/02 |
| WO | 2005/074520 | 8/2005 | |
| WO | 2005/091910 | 10/2005 | |
| WO | 2005/118044 | 12/2005 | A61M 25/00 |
| WO | 2005/118045 | 12/2005 | A61M 25/00 |
| WO | 2005/118050 | 12/2005 | A61M 29/00 |
| WO | 2006/065949 | 6/2006 | A61F 11/10 |
| WO | 2006/074163 | 7/2006 | B01D 71/06 |
| WO | 2006/089178 | 8/2006 | A61M 25/00 |
| WO | 2006/104591 | 10/2006 | A61M 25/00 |
| WO | 2006/105065 | 10/2006 | A61F 2/01 |
| WO | 2006/116636 | 11/2006 | A61F 2/06 |
| WO | 2006/127929 | 11/2006 | A61M 29/00 |
| WO | 2007/035865 | 3/2007 | A61M 27/00 |
| WO | 2007/035885 | 3/2007 | A61L 21/20 |
| WO | 2008/010197 | 1/2008 | A61F 2/01 |

OTHER PUBLICATIONS

Lin, Peter H., et al., "Vena Caval Filters in the Treatment of Acute DVT", *Endovascular Today*, pp. 40-50 (Jan. 2005).

* cited by examiner

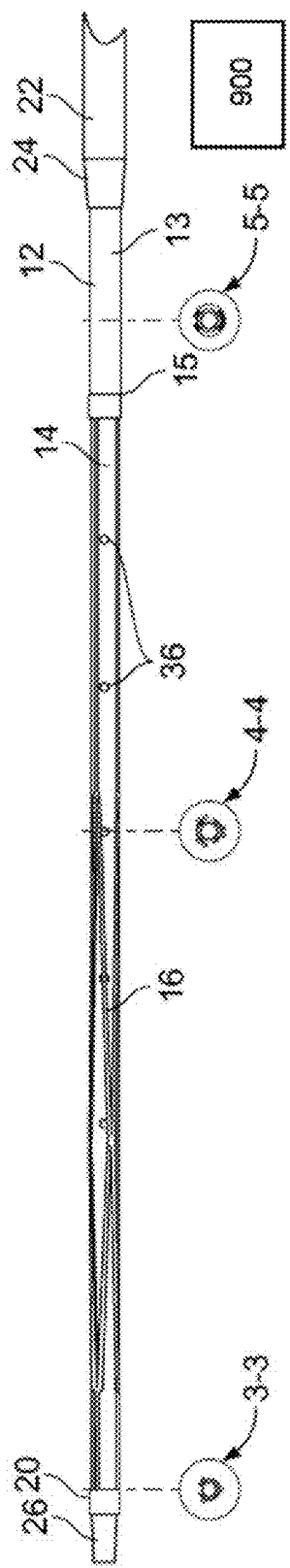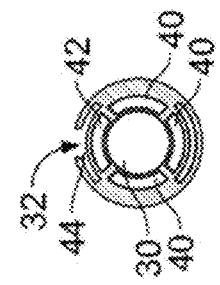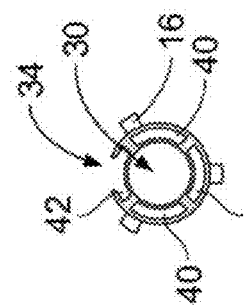

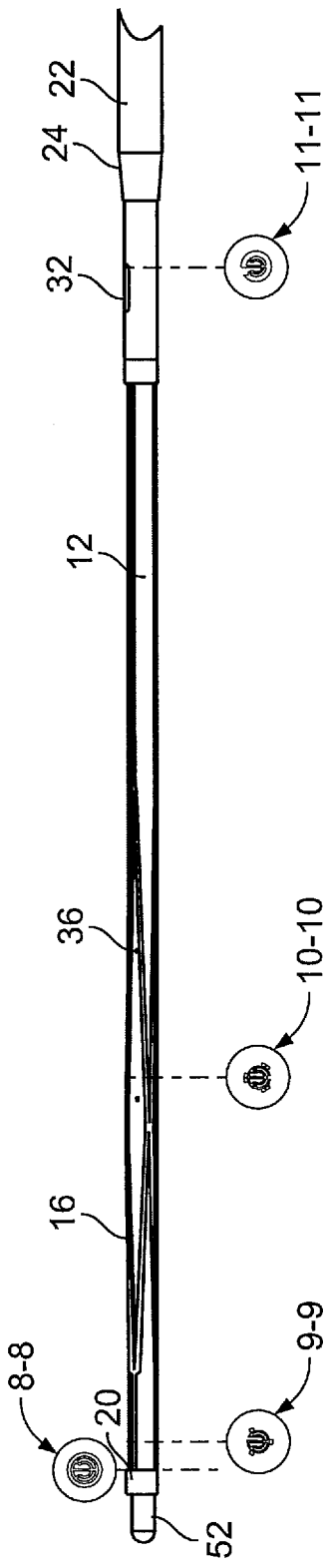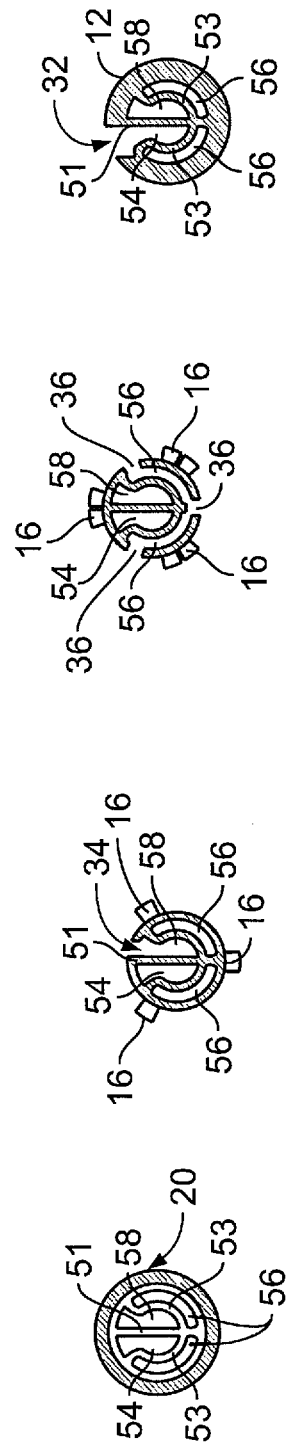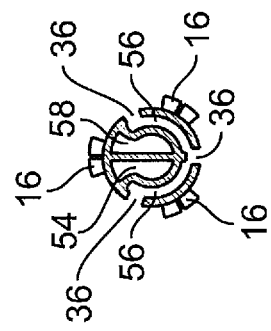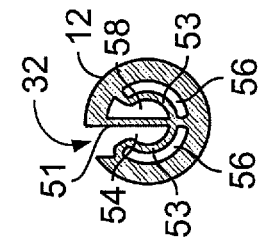
FIG. 7
FIG. 8
FIG. 9
FIG. 10
FIG. 11

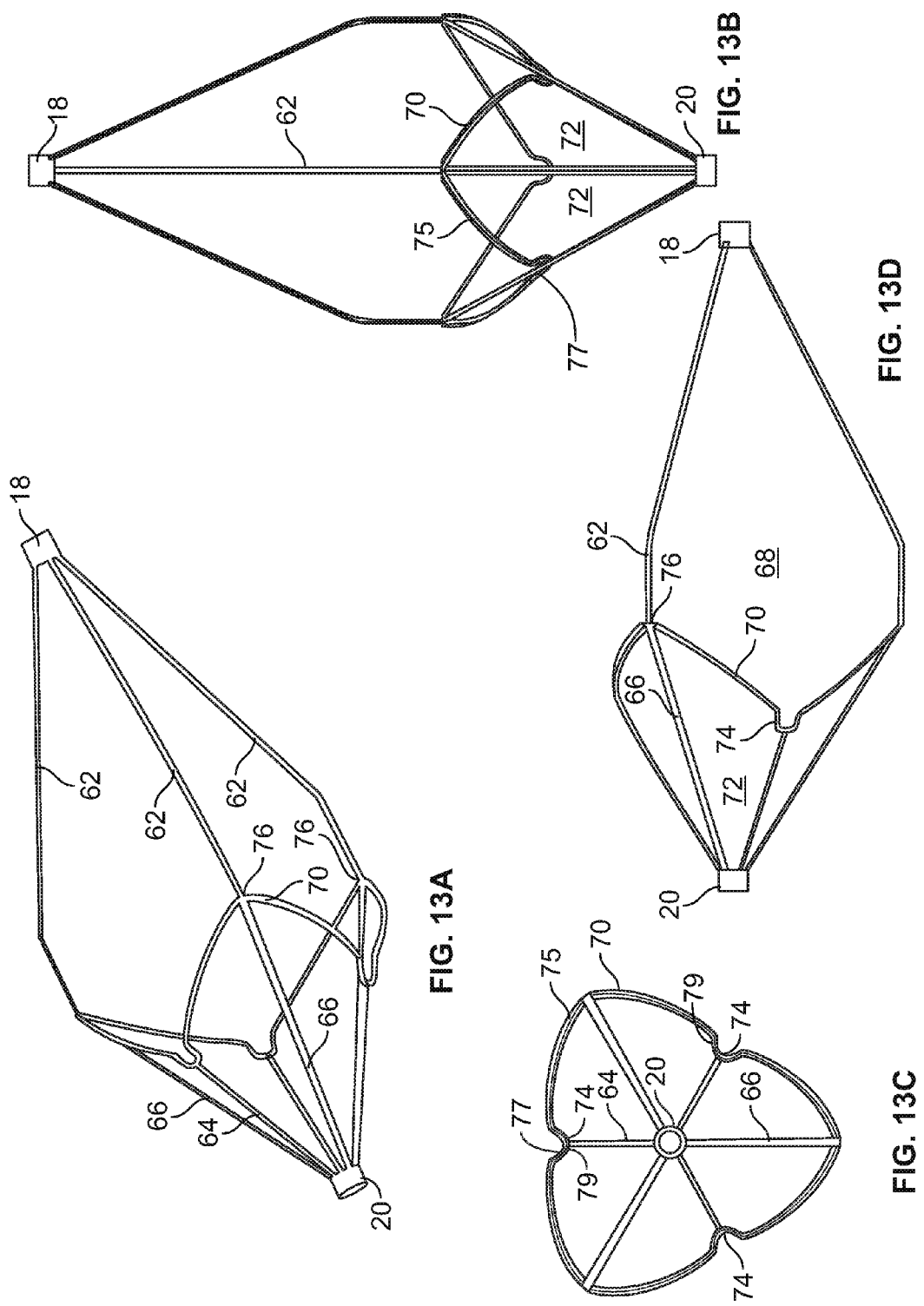

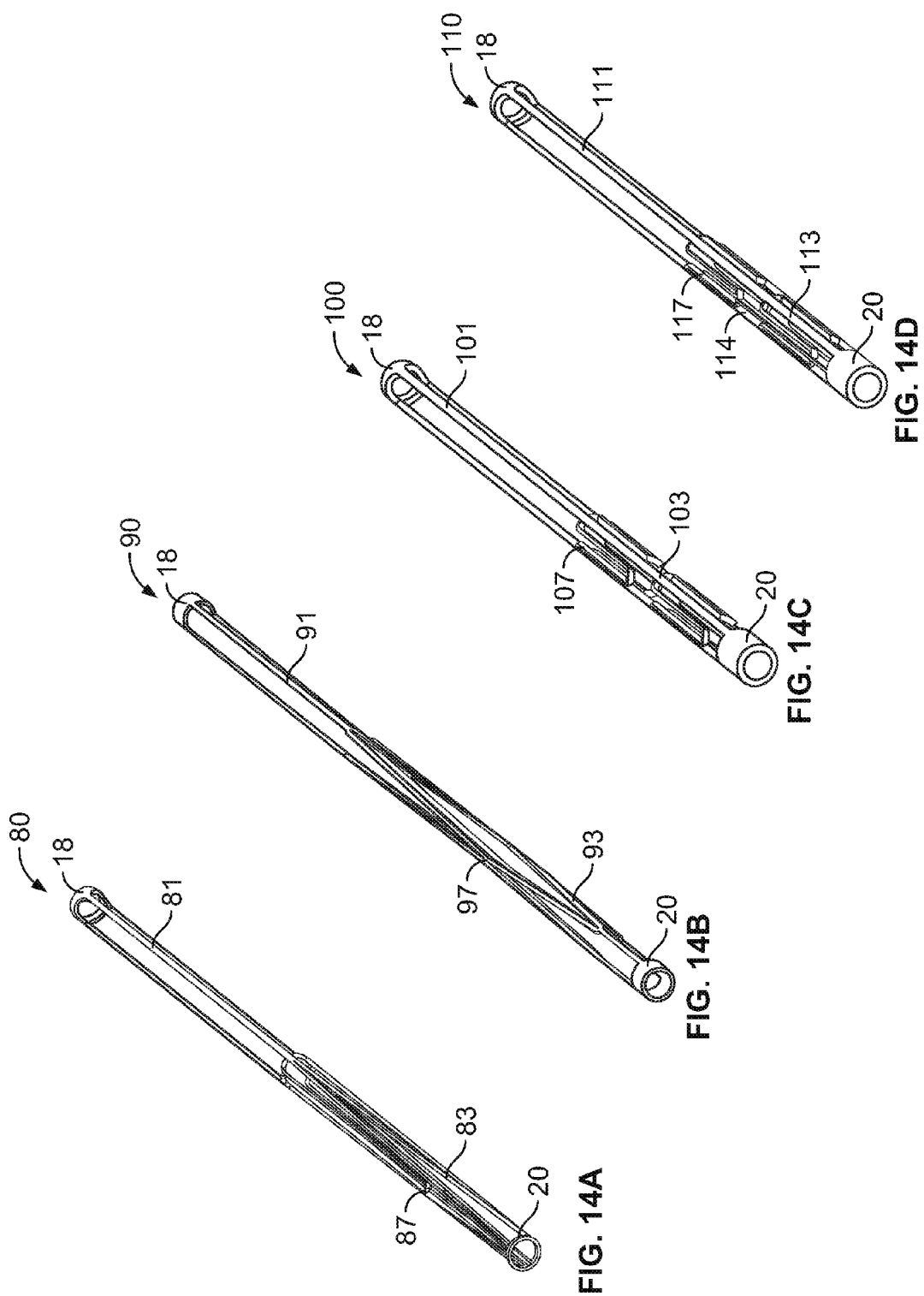

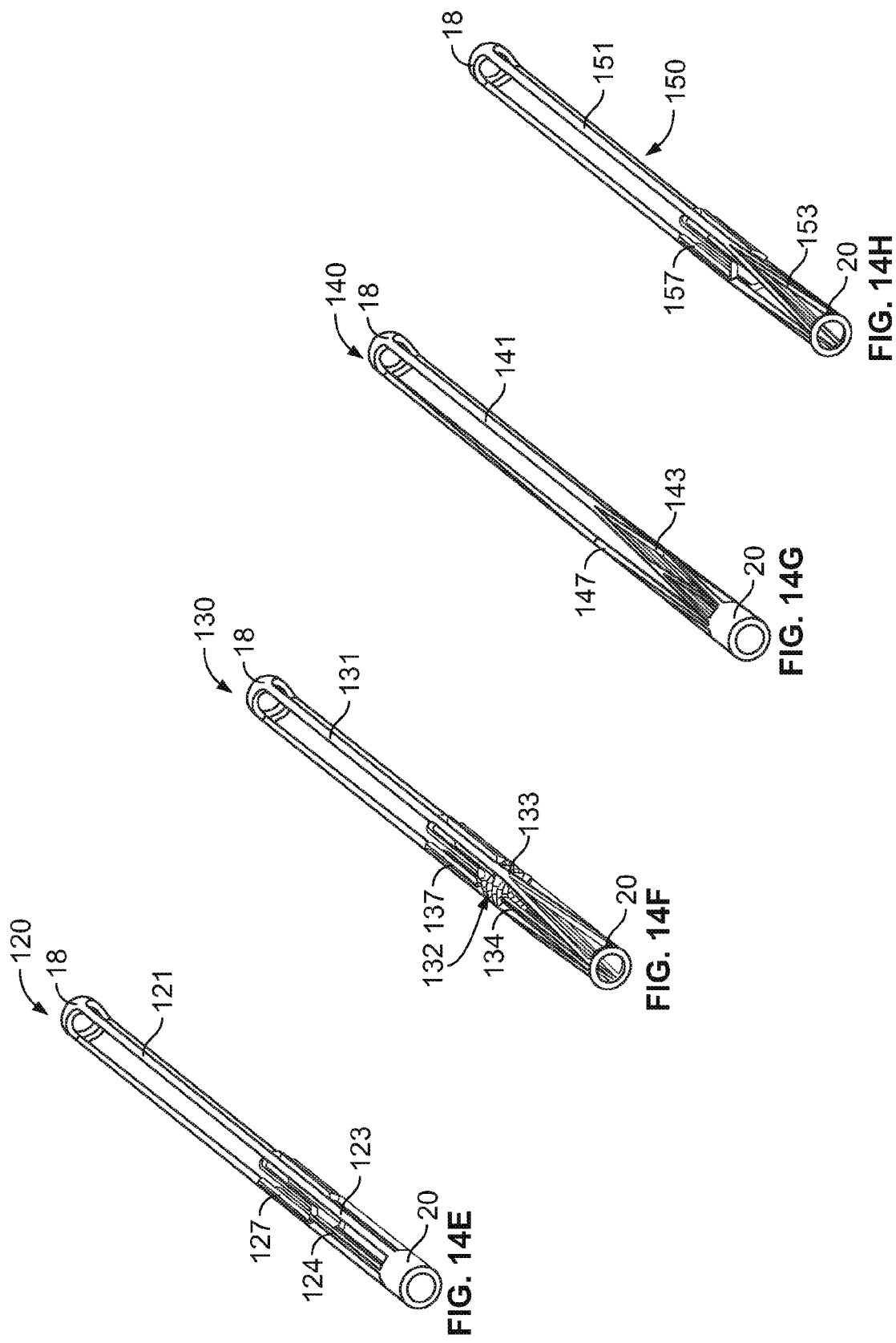

MULTI-LUMEN CENTRAL ACCESS VENA CAVA FILTER APPARATUS AND METHOD OF USING SAME

CROSS-REFERENCE TO RELATED APPLICATIONS

This application is a continuation of U.S. patent application Ser. No. 12/684,839, filed Jan. 8, 2010, which is a continuation-in-part of U.S. patent application Ser. No. 11/849,225 filed Aug. 31, 2007, from which priority is hereby claimed. The aforementioned patent applications are incorporated by reference in their entireties.

BACKGROUND OF THE INVENTION

The present invention pertains generally to the field of vascular filters for capturing embolic material in the blood flow.

The accepted standard of care for patients with venous thromboembolism (VTE) is anticoagulant therapy. Inferior vena cava (IVC) filters are reserved for those patients who fail anticoagulant therapy, or have a complication or contraindication to anticoagulant therapy. Until the early 1970's, the only method of IVC interruption was surgical, either by clipping, ligation or plication. The first clinical experience of an endoluminally-placed device to interrupt IVC flow was reported by Mobin-Uddin et al. in 1969. However, it was not until the introduction of a stainless steel umbrella-type filter by Greenfield et al. in 1973 that an effective method of endoluminally trapping emboli while simultaneously preserving IVC flow became possible. Indeed, for many years, the Greenfield filter set a benchmark by which newer filters were measured. Early generations of filters were inserted by surgical cut-down and venotomy. Eventually filters were able to be inserted percutaneously: initially through large 24 Fr sheaths, though newer generations of filters are able to be delivered through 6 Fr systems.

Despite the safety and efficacy of modern day filters, systemic anticoagulation remains the primary treatment for VTE. Either unfractionated or low molecular weight heparin followed by three months of oral anticoagulation in patients with proximal deep venous thrombosis (DVT) is approximately 94% effective in preventing pulmonary embolism (PE) or recurrent DVT. The routine placement of IVC filters in addition to anticoagulation in patients with documented DVT was investigated by Decousus et al. in a randomized trial. Decousus H, Leizorovicz A, Parent F, et al. *A clinical trial of vena caval filters in the prevention of pulmonary embolism in patients with proximal deep-vein thrombosis*. N Engl J Med 1998; 338:409-415. This study revealed that the use of a permanent filter in addition to heparin therapy significantly decreased the occurrence of PE within the first 12 days compared to those without a filter. However, no effect was observed on either immediate or long-term mortality, and by 2 years, the initial benefit seen in the group of patients with filters was offset by a significant increase in the rate of recurrent DVT.

Despite the efficacy of anticoagulant therapy in the management of VTE, there are certain situations and conditions in which the benefits of anticoagulation are outweighed by the risks of instituting such a therapy. These include contraindications and complications of anticoagulant therapy. In such circumstances, there may be absolute or relative indications for filter insertion Currently, there are eight different types of permanent cava filters that are FDA approved. These include the Bird's Nest filter (Cook Incorporated, Bloomington, Ind.), Vena Tech LGM filter (B. Braun, Bethlehem Pa.), Vena Tech LP (B. Braun), Simon Nitinol filter (Bard, Covington, Ga.), Titanium Greenfield filter (Boston Scientific, Natick Mass.), Over-the-Wire Greenfield filter (Boston Scientific), TrapEase filter (Cordis Corp.) and the Gunther Tulip filter (Cook Inc.)

Well-founded concerns over the long-term complications of permanent IVC filters, particularly in younger patients in need of PE prophylaxis with a temporary contraindication to anticoagulation, has led to the development of temporary and retrievable filters. Temporary filters remain attached to an accessible transcutaneous catheter or wire. These have been used primarily in Europe for PE prophylaxis during thrombolytic therapy for DVT. Currently these devices are not approved for use in the United States. Retrievable filters are very similar in appearance to permanent filters, but with modifications to the caval attachment sites and/or hooks at one end that can facilitate their removal. Retrievable filters are currently available in the United States, examples of these include the Gunther Tulip (Cook Inc.), Opt Ease (Cordis Corp.), and Recovery nitinol filters (Bard Peripheral Vascular, Tempe, Ariz.) Lin P H, et al., *Vena caval filters in the treatment of acute DVT. Endovascular Today* 2005; January: 40-50. The time limit of retrievability is in part dependant on the rate of endothelialization of the device, which typically occurs within 2 weeks. However, differences in design may extend the time period in which the filter may be safely retrieved.

Currently no consensus exists as to which patients have an indication for a retrievable filter. However, it is generally accepted that patients at high risk for pulmonary embolism or with documented PE and with a temporary contraindication to anticoagulation are candidates.

Certain circumstances preclude the placement of a filter in the infrarenal IVC. This includes thrombus extending into the infrarenal IVC, renal vein thrombosis or pregnancy. The safety of suprarenal placement of IVC filters is well documented, with no reported instances of renal dysfunction and no differences in the rates of filter migration, recurrent PE or caval thrombosis.

The rate of upper extremity DVT is on the rise. This is predominantly due to an increasing number of patients having short- and long-term upper extremity central venous access catheters. In one study, 88% of patients found to have an upper extremity DVT had a central venous catheter present at the site of thrombosis at the time of diagnosis or within the previous two weeks. Pulmonary embolism may complicate upper extremity DVT in 12-16% of cases. In patients who have such a complication or contraindication to anticoagulation, a filter can be safely placed immediately below the confluence of the brachiocephalic veins. However, misplacement of an SVC filter is theoretically more likely than with an IVC filter because of the relatively short target area for deployment.

The most common imaging modality used for filter insertion is fluoroscopy, performed either in an interventional suite or an operating room. Bedside placement of filters has inherent advantages, particularly for critically ill patients in intensive care settings where transport can be avoided. Portable fluoroscopy, surface duplex ultrasound and intravascular ultrasound (IVUS) have all been used to assist with bedside filter placement.

Vena cava filter placement frequently occurs concomitantly with central access line placement or in critically ill patients that already have a central access line in place. Heretofore, however, there have been no devices which combine the function of a central access catheter and a removable vena cava filter.

SUMMARY OF THE INVENTION

A multi-lumen central access catheter comprises a proximal end and a distal end thereof relative to the longitudinal axis of the catheter, a vena cava filter near the distal end of the central access catheter, at least one of a port proximal the vena cava filter or a port distal the vena cava filter and plural fluid infusion ports passing through walls of the central access catheter and positioned to deliver fluid to a space delimited by the vena cava filter. The plural fluid infusion ports are positioned in the walls of the central access catheter and have a directional flow orientation such that any or all regions of the space delimited by the vena cava filter may be exposed to fluid flow there from. The proximal and distal ports, which may be positioned entirely or partially distant from an open area bounded by the filter member, permit measuring pressure and/or flow velocity across the filter as a determinant of extent of capture of embolic material in the filter or for measuring flow rate at the position of the filter member as a positional indicator within the body. Pressure or flow sensing may be accomplished by a hydrostatic fluid column in communication with each of the proximal and distal ports and a pressure transducer operably associated with a proximal end of the central access catheter. Alternatively, pressure or flow sensors may be disposed either within the proximal and distal ports or within lumens communicating with the proximal and distal ports. Preferably, the proximal and distal ports, and lumens associated therewith, are also open to fluid flow to provide means for introducing fluids, such as an anticoagulant, thrombolytic or other bioactive agents, contrast medium, blood transfusions, intravenous fluids or other medications. Alternatively, the proximal and distal ports may be used for withdrawal or evacuation of fluids or other material through the catheter. The multiple infusion ports also provide a means for introducing a flushing medium, such as saline, under elevated pressure to produce mechanical thrombolysis or induce thrombolysis by the infusion of thrombolytic agents directly to thrombus within the filter.

The present invention may be configured for either a femoral approach or a jugular approach to the inferior vena cava. Vena cava filters are typically deployed infrarenaly, but may also be deployed suprarenaly. It will be understood that within the inferior vena cava blood flow is superior, i.e., toward the patients head. Thus, in all embodiments, the vena cava filter will be positioned so that it opens inferiorly, i.e., away from the patient's head and toward the direction of the blood flow. It will be appreciated, therefore, that in the present invention, the vena cava filter will have a different axial orientation on the central access catheter depending upon whether the device is intended for use in a femoral approach or a jugular approach.

Accordingly, it is an objective of the present invention to provide a multi-lumen catheter coupled to a vena cava filter that is useful both as a central venous access catheter for administration of intravenous fluids, bioactive agents, contrast agents, flushing agents, pressurized fluids for mechanical thrombolysis and/or withdrawal of blood samples and for capture of thrombus or emboli.

Another aspect of the present invention is to provide a filter geometry in which the proximal portion of the filter, relative to the axis of blood flow, has larger interstitial openings to permit thrombus or embolic material to flow into the filter, while the distal portion of the filter, again relative to the axis of blood flow, has relatively smaller interstitial openings that capture the thrombus or embolic material within the filter. Another way to view this aspect is that the structure of the filter includes a greater open surface area exposed to the flow of embolic material into the filter at its proximal end, while the distal end has smaller open surface area exposed to the flow of embolic material to capture the embolic material in the distal end of the filter member. More specifically, regardless of whether the present invention is delivered by a jugular approach or a femoral approach, the filter geometry is such that the larger interstitial openings of the filter are positioned inferiorly along a longitudinal axis of the filter.

BRIEF DESCRIPTION OF THE DRAWINGS

FIG. 2 is a side elevational view of a central venous access vena cava filter catheter in accordance with the first embodiment of the present invention.

FIG. 3. is a cross-sectional view taken along line 3-3 of FIG. 2.

FIG. 4 is a cross-sectional view taken along line 4-4 of FIG. 2.

FIG. 5 is a cross-sectional view taken along line 5-5 of FIG. 2.

FIG. 7 is a side elevational view of a central venous access vena cava filter catheter in accordance with the second embodiment of the present invention.

FIG. 8 is a cross-sectional view taken along line 8-8 of FIG. 7.

FIG. 9 is a cross-sectional view taken along line 9-9 of FIG. 7.

FIG. 10 is a cross-sectional view taken along line 10-10 of FIG. 7.

FIG. 11 is a cross-sectional view taken along line 11-11 of FIG. 7.

FIG. 13A is a perspective view of a vena cava filter member in accordance with a first embodiment thereof.

FIG. 13B is a first side elevational view thereof.

FIG. 13C is an end elevational view thereof.

FIG. 13D is a second side elevational view thereof.

FIGS. 14A-14H are perspective views of alternative embodiments of a vena cava filter member in accordance with the present invention.

DETAILED DESCRIPTION OF THE PREFERRED EMBODIMENTS

Figure 16A:
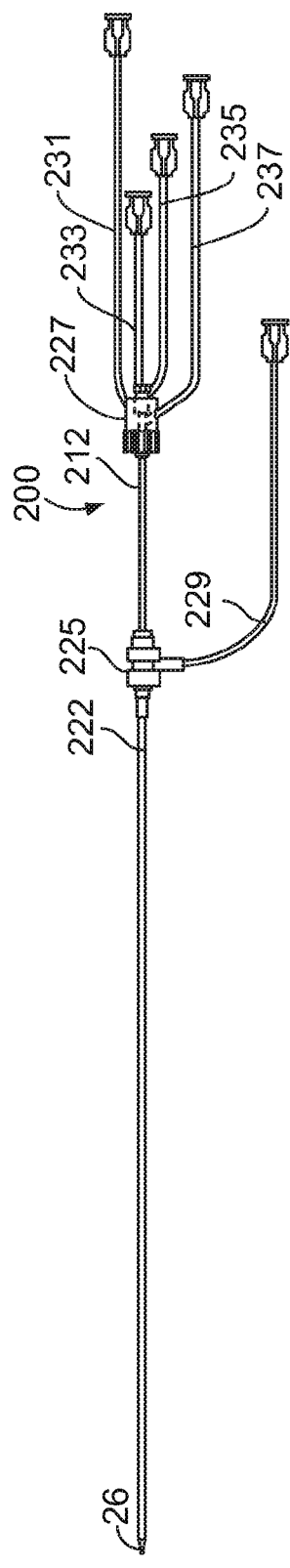
FIG. 16A is a side elevational view of the vena cava central line catheter in its undeployed state.
Figure 16B:
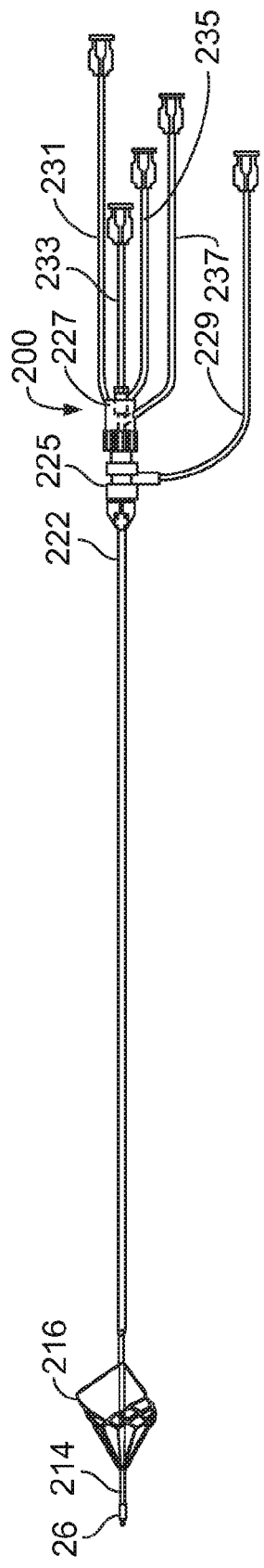
FIG. 16B is a side elevational view of the vena cava central line catheter in its deployed state.

In the accompanying Figures like structural or functional elements are designated by like reference numerals, e.g., 16, 116, 216, 316, 416 represent similar structural or functional elements across different embodiments of the invention. With particular reference to FIGS. 1-5, according to a first embodiment of the invention, there is disclosed a central venous access filter ("CVAF") 10 that is composed generally of a multi-lumen central venous access catheter body 12 having a proximal port 32 associated with a first lumen 44 and a distal port 34 associated with a second lumen 42, a filter member 16, having a first end 18 and a second end 20, is positioned generally intermediate the distal port 34 and the proximal port 32 and is generally concentric relative to the catheter body 12. An outer sheath 22 is concentrically disposed over the catheter body 12 such that relative movement of the catheter body 12 and the outer sheath 22 either exposes the filter member 16 or captures the filter member 16 within the outer sheath 22. The outer sheath 22 terminates in an annular opening at a distal end thereof and at first hub member 225 as depicted in FIGS. 16A and 16B. The proximal hub 225 will be described more fully hereinafter. The catheter body 12 extends through a central bore in the proximal hub 225 and passes through a central lumen of the outer sheath 22. A second hub member 227, as depicted in FIGS. 16A and 16B, is coupled to a proximal end of the catheter body 12. The second hub member 227 and the first hub member 225 are removably engageable with each other as will also be described further hereinafter.

Depending upon the orientation of the filter member 16, the first end 18 or the second end 20 may either be fixed or moveable relative to the catheter body 12. Alternatively, as will be discussed further hereinafter, the filter member 16 may have only a first end 18 which is fixed to the catheter body 12

To facilitate percutaneous introduction of the inventive CVAF 10, a physician may optionally elect to employ an introducer sheath (not shown) as vascular access conduit for the CVAF 10. The presence of the filter member 16 at the distal end of the catheter body 12 creates a region of relatively lower flexibility and the practitioner may determine it beneficial to employ an introducer sheath for vascular access.

As used in this application, unless otherwise specifically stated, the terms "proximal" and "distal" are intended to refer to positions relative to the longitudinal axis of the catheter body 12. Those skilled in the art will understand that the catheter body 12 has a distal end which is first inserted into the patient and a proximal end which opposite the distal end. Additionally, the terms "inferior" or "inferiorly" are intended to refer to the anatomic orientation of being in a direction away from the patient's head while the terms "superior" or "superiorly" are intended to refer to the anatomic orientation of being toward the patient's head.

The multi-lumen aspect of the inventive central venous access filter catheter 10 is shown more clearly in FIGS. 2-5. The catheter body 12 has a proximal section 13 and a distal section 14. which is longitudinally opposite the proximal section 13, and which may have a relatively smaller diametric profile than the proximal section 13. As described above, the first lumen 44 terminates at the proximal port 32, while the second lumen 42 terminates at the distal port 34. A central guidewire lumen 30 may be provided that extends the entire longitudinal length of the catheter body 12 and terminates at the distal end of the catheter body 12 at a distal guidewire opening 31 that permits the catheter body to track along a guidewire during a procedure. The central guidewire lumen 30 may also be used to introduce fluids, such as bioactive agents, intravenous fluids or blood transfusions.

Additionally, at least one of a plurality of infusion lumens 40 are provided, each having at least one infusion port 36 that passes through a wall of the catheter body 12. Bioactive agents, flushing fluids for flushing or under elevated pressures for mechanical thrombolysis of thrombus in the filter member 16, contrast agents or other fluids may be infused through the infusion lumens 40 and out of the at least one infusion port 36 to pass into the patient's venous system for either local or systemic effect. In accordance with one embodiment of the invention, plural infusion ports 36 are provided with multiple ports 36 being provided in communication with a single infusion lumen 40 and spaced along a longitudinal axis of the catheter body 12. Additionally, plural infusion ports 36 may be provided in a circumferentially spaced manner to provide for fluid infusion at points spaced around the circumference of the catheter body 12. In this manner, fluid infusion is provided along both the longitudinal axis and the circumferential axis of the catheter body 12 within the spatial area defined by and bounded by the filter member 16. Because the plural infusion ports 36 communicate with the spatial area defined by and bounded by filter member 16, fluids introduced through the infusion lumens 40 are directed immediately at thrombus caught within the filter member 16. This permits thrombolytic agents, high pressure mechanical thrombolysis using a pressurized saline flush to be introduced directly to the situs of thrombus capture within filter member 16. Alternatively, thermal, ultrasound or other types of thrombolysis may be employed to disrupt thrombus captured by the filter member 16. For example, the annular space between the outer sheath 22 and the catheter body 12 may be used to introduce a thrombolytic to the filter and shower the filter to disrupt thrombus caught by the filter member 16. Additionally, the balloon depicted in FIGS. 21 and 22 may be positioned adjacent the filter member 16 and be provided with plural openings oriented in the direction of the filter member 16 to facilitate thrombolysis.

It will be understood, by those skilled in the art, that alternative arrangements of the first lumen 44, the second lumen 42, the guidewire lumen 30, or the infusion lumens are possible and contemplated by the present invention. The number and arrangement of lumens in the catheter body 12 is a function of the desired number of operable ports passing through the walls of the catheter body 12, the relative position of the operable ports, the desired position and geometry of the guidewire lumen 30, the desired longitudinal flexibility of the catheter body 12, the desirable degree of kink resistance of the catheter body 12, and other factors which are known to one of ordinary skill in the catheter arts.

While the present invention is not limited to specific dimensional sizes of either the catheter body member 12, the outer sheath 22, lumen diameter or port dimension, an exemplary outer diameter size of the outer sheath 22 is between 8 Fr (2.7 mm) and 9 Fr (3.0 mm) while an exemplary outer diameter size of the catheter member 12 is between 6 Fr (2.0 mm) and 7 Fr. A diametric transition taper 15 may be provided between the proximal portion 13 and the distal portion 14 of the catheter body 12 corresponding to the thickness of the filter member 16. In this manner, the outer surface of the filter member 16 is substantially co-planar with the outer diameter of the proximal portion 13 of the catheter body 12 about its entire circumference. Alternatively, the catheter body member 12 may have a constant diameter and the filter member 16 coupled to an outer surface of the catheter body member 12, with the outer sheath 22 having a luminal diameter sufficient to fit over the filter member 16. Moreover, the fixed first end 18 of filter 16 is positioned adjacent and in abutting relationship with the diametric transition 15, while the moveable second end 20 of filter member 16 is concentrically positioned around the distal section 14 of catheter body 12 and is reciprocally moveable thereupon to accommodate diametric expansion of the filter member 16. Lumen diameter and port dimension are a function of design requirements and are variable depending upon the desired purpose and function of the lumen or port, e.g., pressure sensing, infusion, evacuation, guidewire, flow sensing, or flow conduit.

In order to aid a physician in visualizing the CVAF 10 in vivo with an imaging system 900, at least one radio-opaque or other viewable marker may be provided. A first marker 24 is provided at the distal end of the outer sheath 22 and a second marker 26 may be provided at a distal tip 33 of the catheter body 12. It will be understood that when the outer sheath 22 is in its non-retracted delivery position, that the filter 16 will be covered and the marker 24 and the second marker 26 will be adjacent or in close proximity with one another. Alternatively, the outer sheath 22 may, itself, be made of or include a radio-opaque or other viewable material, such as a metal braid or metal reinforcement within or applied to a polymeric sheath. The first and second markers 24, 26 or the material of the outer sheath 22 may enhance visualization of the CVAF 10 under fluoroscopy, ultrasound or other visualization or guidance technique.

FIGS. 6-11 illustrate a second embodiment of the CVAF 50. Unlike CVAF 10, CVAF 50 does not include the central guidewire lumen 30 of CVAF 10. Rather, while the general construct of CVAF 50 is similar to that of CVAF 10, a different configuration of the inner lumens is employed.

CVAF 50, like CVAF 10, consists generally of a multi-lumen central venous access catheter body 12 having a proximal port 32 associated with a first lumen 54 and a distal port 34 associated with a second lumen 58, a filter member 16, having a fixed first end 18 and a moveable second end 20, is positioned generally intermediate the distal port 34 and the proximal port 32 and is generally concentric relative to the catheter body 12. Use of the term "generally intermediate" is intended to mean that at least a substantial portion of the filter member 16 resides intermediate the distal port 34 and the proximal port 32. Thus, the filter member 16 may partially overlay either or both of the proximal port 32 or the distal port 34.

The catheter body 12 has a proximal section 13 and distal section 14, which is longitudinally opposite the proximal section 13 which may have a relatively smaller diametric profile than the proximal section 13. As described above, the first lumen 54 terminates at the proximal port 32, while the second lumen 58 terminates at the distal port 34. An atraumatic tip 52 terminates the catheter body 12 at its distal end.

The atraumatic tip 52 preferably includes a radio-opaque marker to aid in positional visualization of the distal end of the catheter body 12.

A plurality of infusion lumens 56 are provided, each having at least one infusion port 36, preferably plural infusion ports 36, that passes through a wall of the catheter body 12 and communicates with a space defined within an area bounded by the filter member 16. Bioactive agents, flushing fluids, pressurized mechanical thrombolytic fluids, or other fluids may be infused through the infusion lumens 56 and out of the at least one infusion port 36 to pass into the space defined by the filter member 16 and ultimately into the patient's venous system for either local or systemic effect. In accordance with one embodiment of the invention, the each of the plural infusion lumens 56 are in fluid communication with plural ports 36 arrayed along both the longitudinal axis and the circumferential axis of the catheter body. This configuration provides for fluid infusion along both the longitudinal axis and the circumferential axis of the catheter body 12 and in direct communication with the space defined by the filter member 16 that captures thrombus.

The infusion lumens 56, the first lumen 54 and the second lumen 58 are bounded by and separated from each other by first catheter septum 51 and second catheter septum 56 which also aid in providing structural support for the catheter body 12. First catheter septum 51 is a generally diametrically and longitudinally extending member that divides the first lumen 54 from the second lumen 58 along the longitudinal axis of the catheter body 12. Second catheter septum 56 may comprise a generally U-shaped member that intersects the first catheter septum 51 at a lower aspect of the septum and is connected with an inner wall surface of the catheter body 12 at upper aspects of the septum 51 to define two infusion lumens in lateral regions of the catheter body 12.

The filter member 16 has two general configurations. A first configuration consists generally of two opposing generally open conical sections formed by plural interconnected structural elements defining the lateral surfaces of each open conical section, wherein the two opposing generally open conical sections each have open bases facing each other which are interconnected by a generally cylindrical section of the filter member 16. Each open conical section has an open base and an apex, wherein the apices project in opposing directions, with one apex projecting proximally and another apex projecting distally relative to the axis of the catheter. The plural interconnected structural elements forming the lateral surfaces of each generally open conical sections may be strut-like structural members extending generally axially along the longitudinal axis of the filter member 16. The axially extending strut-like structural members may be linear members or may be curved members. The apices of each of the generally open conical sections are formed either of a generally cylindrical collar that serves to couple the filter member 16 to the catheter body 12. The generally cylindrical collar is concentrically engaged about the catheter body 12 and may be axially movable thereupon, or is formed by connections between adjacent pairs of longitudinal strut-like structural members which circumscribe a circumference of the catheter body 12. The generally cylindrical section of the filter member 16 is formed by a generally open lattice of interconnected structural elements which connect the base of a first open conical section to the base of a second open conical section. The generally cylindrical section of the filter member 16 lies in apposition with a vascular wall upon deployment of the filter member 16 with a vascular lumen.

A second general configuration of the filter member 16 consists generally of a single generally open conical section in which a plurality of longitudinal strut-like structural members form the lateral surfaces of the conical section and are connected to a generally cylindrical collar which couples the filter member 16 to the catheter body 12 at an apex of the generally open conical section. The base of the generally open conical section is formed by opposing ends of the longitudinal strut-like structural members. A generally cylindrical section of the filter member 16, formed of a generally open lattice of interconnected structural elements, extends from the longitudinal strut-like structural members forming the base of the generally open conical section, to provide a region of the filter member 16 which is in apposition to the vascular wall upon deployment of the filter member.

Figure 1:
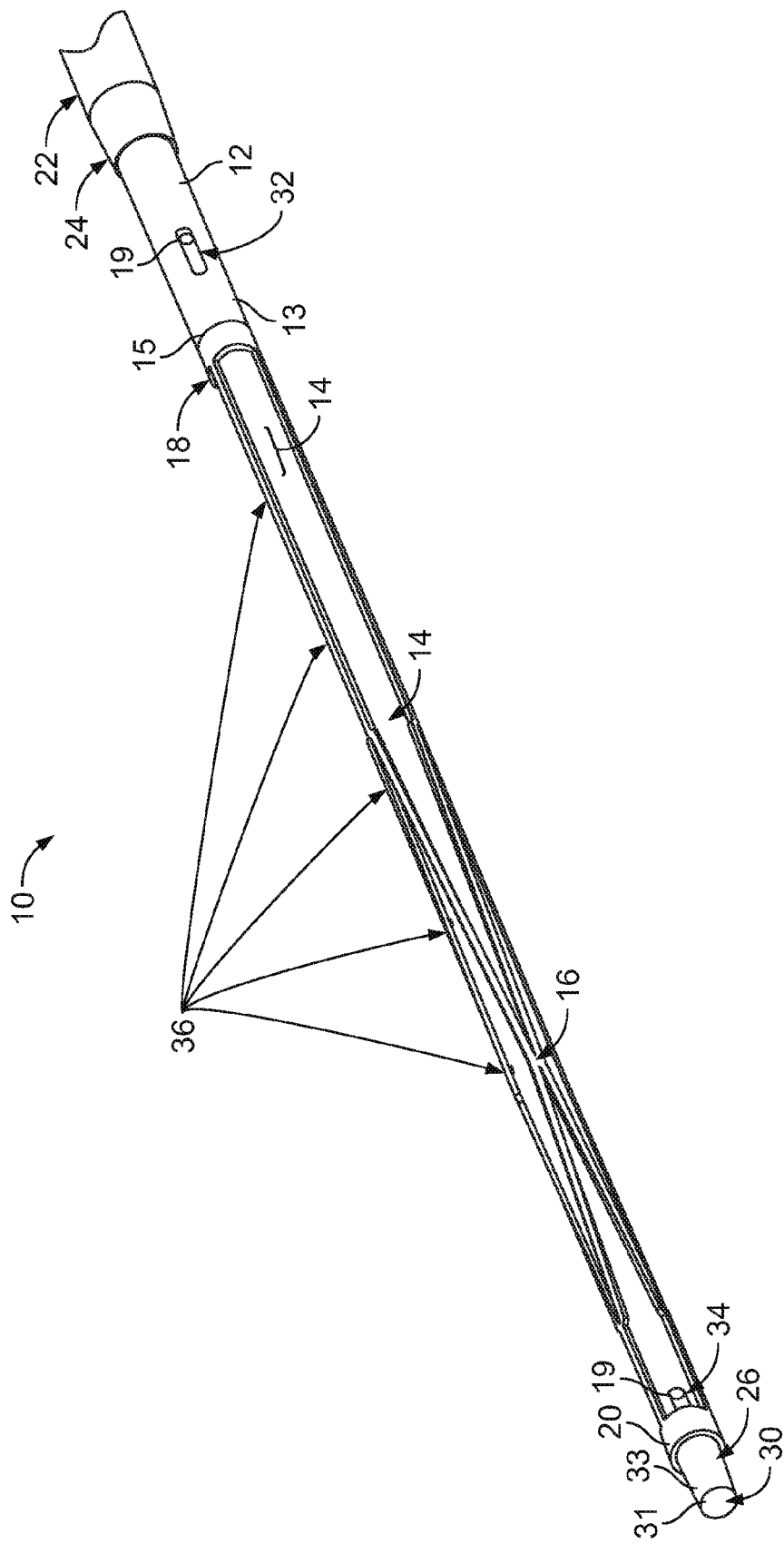
FIG. 1 is a perspective view of a central venous access vena cava filter catheter in accordance with a first embodiment of the present invention with the vena cava filter in an unexpanded state.
Figure 6:
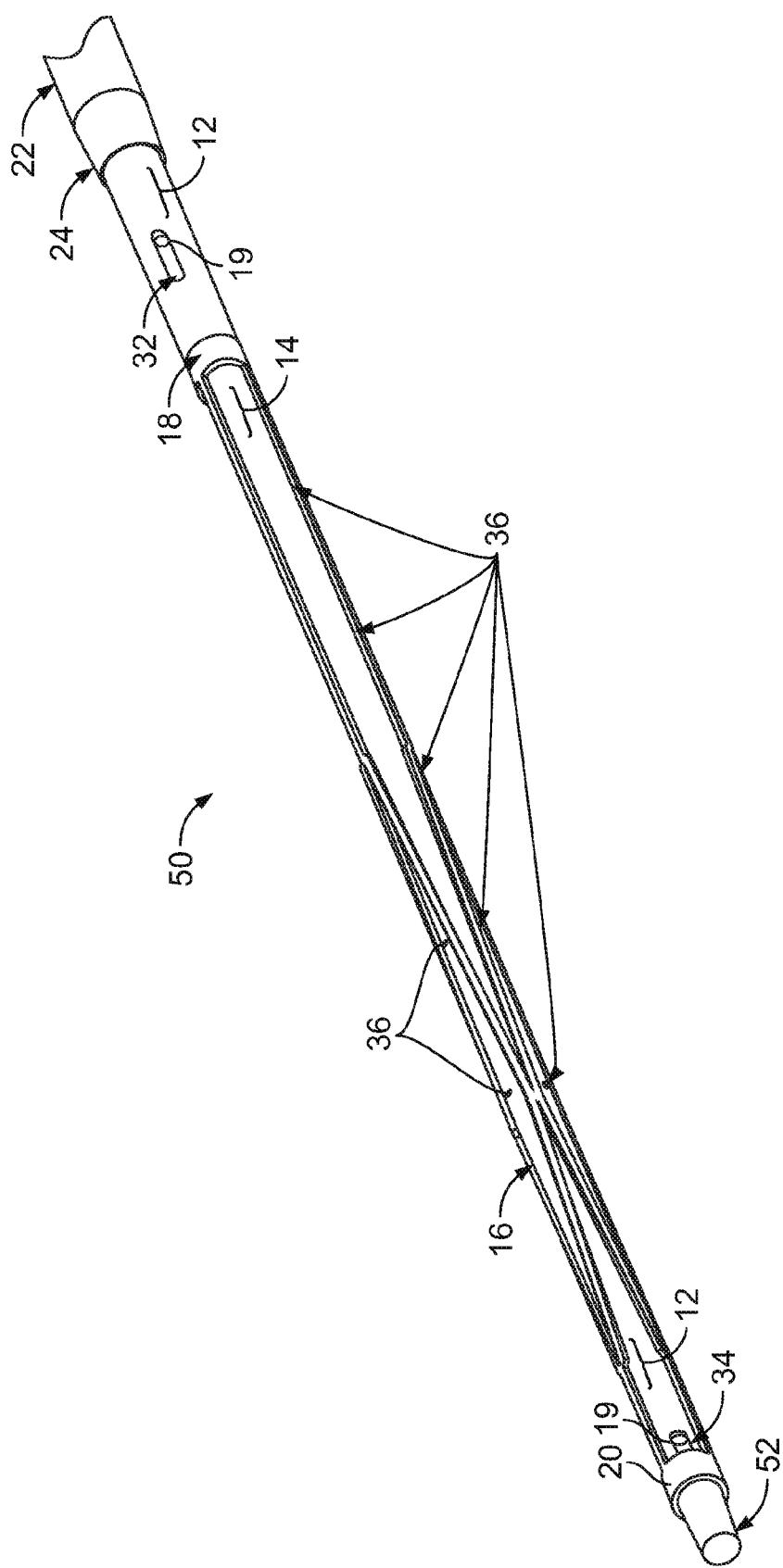
FIG. 6 is a perspective view of a central venous access vena cava filter catheter in accordance with a second embodiment of the present invention illustrating the vena cava filter in an unexpanded state.
Figure 12:
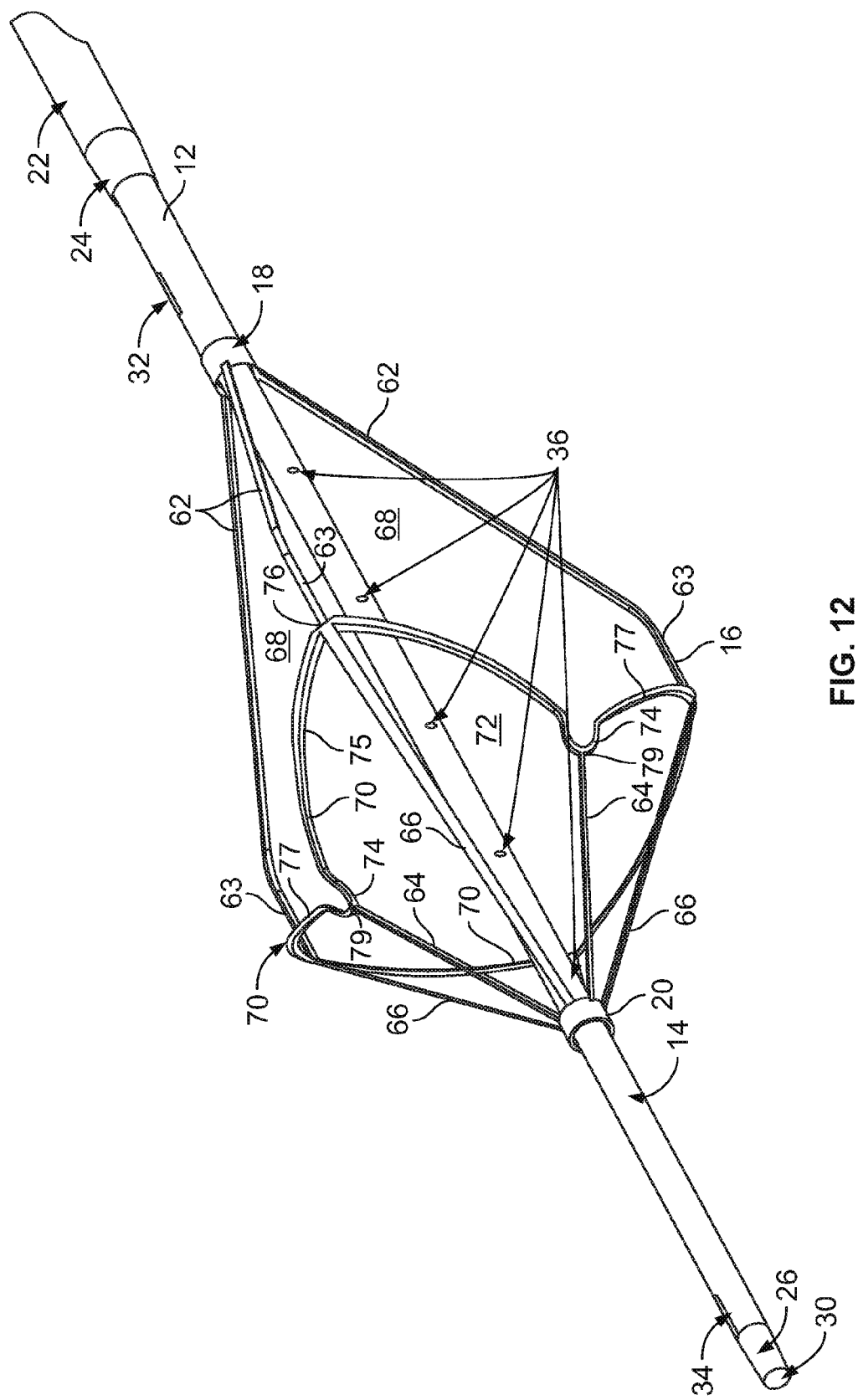
FIG. 12 is a perspective view of the central venous access vena cava filter catheter of FIG. 1 illustrating the vena cava filter in a diametrically expanded state.
Figures 15A, 15B, 15C, 15D, 15E, 15F, 15G, 15H:
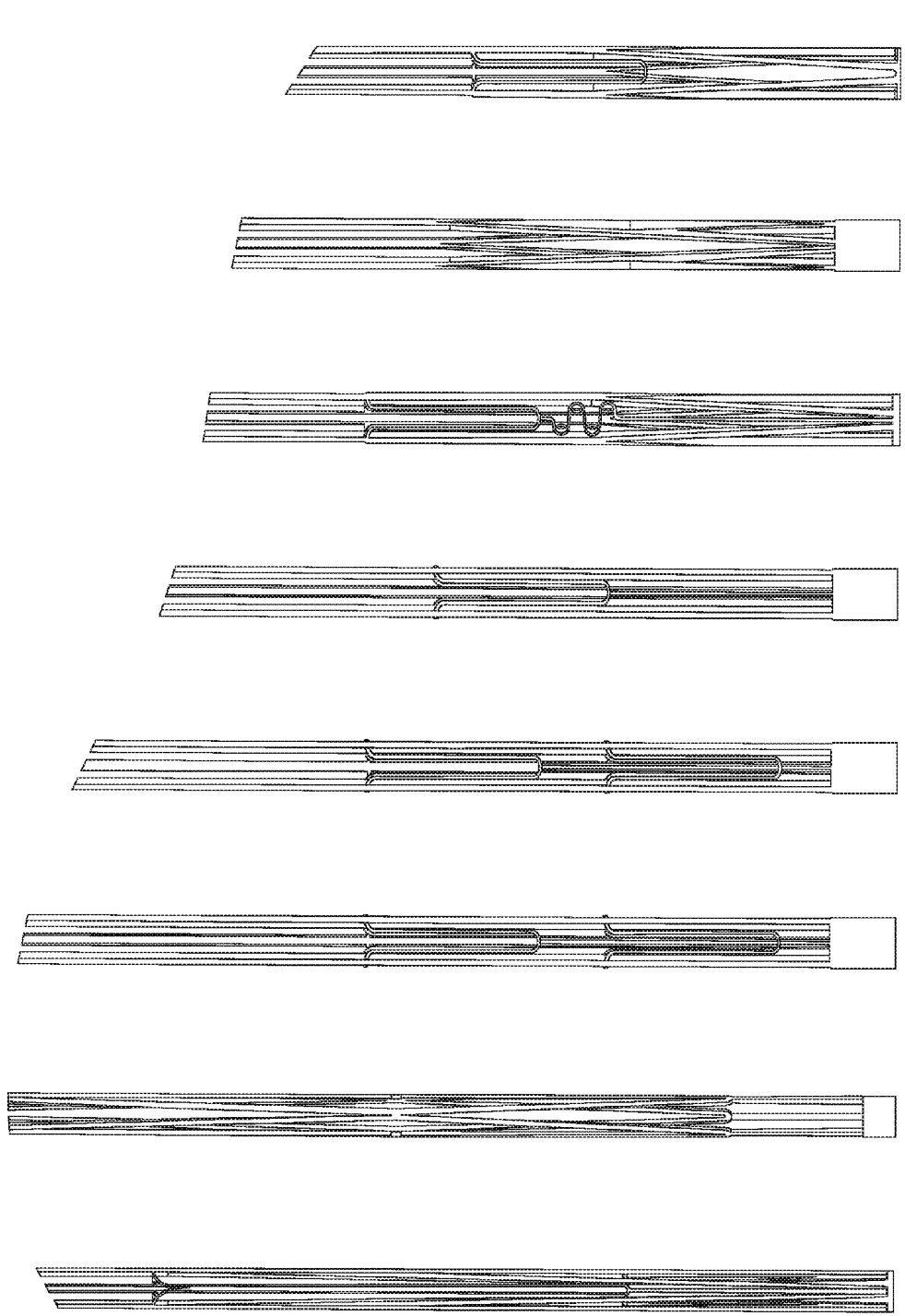
FIG. 15A-15H are fragmentary side elevational views of the alternative embodiments of the vena cava filter member illustrated in FIGS. 14A-14H.

One embodiment of the filter member 16 is illustrated in its diametrically expanded configuration in FIGS. 12-13D. In this embodiment, filter member 16 consists generally of a first end 18 and a second end 20, each of which consists generally of a tubular structure which is circumferentially positioned about a section of the catheter body 12. One of the first end 18 and second end 20 are fixedly coupled to the catheter body 12, while the other is movable relative to the catheter body 12. At least one of a plurality of first strut members 62, are coupled at their first end to the first end 18 of filter member 16 and each extends axially relative to the longitudinal axis of the catheter body 12. Each of the first strut members 62 is an elongate member that, upon diametric expansion of the filter member 16, flares away from the central longitudinal axis of the catheter body 12, in a generally tapered conical manner, and terminates in an end section 63 that bends generally parallel to and along the longitudinal axis of the catheter body 12. A plurality of second strut members 64 are coupled at an end to the second end 20 of filter member 16 and each extends parallel relative to the longitudinal axis of the catheter body 12. A plurality of third strut members 66 are coupled at ends thereof to the an end of the filter member and each extends parallel relative to the longitudinal axis of the catheter body 12. It will be appreciated, by those skilled in the art, that the number of struts employed as the first strut members 62, the second strut members 64 and the third strut members 66 forming the filter member 16 may be evenly distributed about a 360 degree circumference and define the lateral wall surfaces of the filter member 16. A circumferential member 70 extends circumferentially to define a circumferential axis of the filter member 16 and has a series of continuous undulations defining peaks a series of peaks 75 and valleys 77 about the circumference of filter member 16. Each of the plurality of first strut members 62, the plurality of second strut members 64 and the plurality of third strut members 66 are coupled to the circumferential member 70 at different points about its circumferential axis and intermediate the proximal end 18 and the distal end 20 of the filter member 16. In its unexpanded state the filter member 16 has a generally tubular shape, while in its expanded state the filter member 16 assumes one of the general configurations discussed above, i.e., either oppositely extending generally open conical sections or a single generally open conical section.

The plurality of first strut members 62 are preferably offset from each other by approximately 120 degrees about the circumference of the catheter body 12. The plurality of second strut members 64 are also preferably offset from each other by approximately 120 degrees. Finally, the plurality of third strut members 66 are also preferably offset from each other by approximately 120 degrees. Each of the plurality of first strut members 62 couple at a junction 76 to the circumferential member 70 at a peak thereof. Similarly, each of the plurality of third strut members 66 couple at junction 76 to the circumferential member 70 at a peak thereof. In this manner, a first strut member 62 and a third strut member 66 are each coupled to circumferential member 70 at junction 76 and, in this relationship, form a generally linear member that extends along the longitudinal axis of the catheter body and connects between the proximal end 18 of the filter member 16 and the distal end 20 of the filter member 16. Each of the second strut members 64 couple, at their proximal ends to a valley 77 of the circumferential member 70 and connects at a junction 79. Unlike the connections at junction 76 between the plurality of first strut members 62 and the plurality of second strut members, in this embodiment of the filter member 16, there is no member that connects to junction 79 and extends from the first end 18 of the filter member 16. In this configuration, the circumferential member 70 assumes a generally circumferential tri-leaflet ring having three peaks 75 and three valleys 77 which circumferentially circumscribe a central opening 72 which faces inferiorly relative to the patient's blood flow such that the blood flow first passes into the central opening 72 and past the third strut members 66 and the second strut members 64 then past the first strut members 62.

To facilitate bending and folding of the circumferential member 70 between the expanded and unexpanded states, generally U-shaped hinge members 74 may be provided at each of the valleys 77 of the circumferential member 70. It will be understood that each of the plurality of first strut members 62, plurality of second strut members 64, plurality of third strut members 66 and the circumferential member 70 are preferably fabricated of biocompatible materials, such as shape memory alloys, superelastic materials or elastic materials, including, without limitation, titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, cobalt-chromium-molybdenum alloys, nitinol, and stainless steel.

FIGS. 14A-14H and corresponding FIGS. 15A-15H depict alternative embodiments of the filter member 16, labeled 80, 90, 100, 110, 120, 130, 140 and 150, respectively. Like filter member 16, each of filter members 80, 90, 100, 110, 120, 130, 140 and 150 having a first end 18 and a second end 20 that each consist of a generally ring-like structure intended to circumferentially couple to a catheter body 12 (not shown), with the first end 18 being fixed and the second end 20 being reciprocally moveable axially along the distal portion 14 of catheter body 12. Like filter member 16, each of the alternative filter member embodiments depicted in FIGS. 14A-14H and 15A-15H, consist of a plurality of first strut members 81, 91, 101, 111, 121, 131, 141 and 151, respectively, extending distally from the first end 18 of the filter member and a plurality of second strut members 83, 93, 103, 113, 123, 133, 143 and 153, respectively, extending proximally from the distal end 20 of the filter member, with a diametrically expansible circumferential member 87, 97, 107, 117, 127, 137, 147, 157, respectively, interconnecting the distally extending strut members 81, 91, 101, 111, 121, 131, 141 and 151, respectively, with the proximally extending strut members 83, 93, 103, 113, 123, 133, 143 and 153. In the alternative embodiments of filter members 100, 110 and 120, at least some distally extending strut members and at least some of the proximally extending strut members form linear elements that extend along the entire longitudinal axis of the respective filter member, with the circumferential member being comprised of at least one undulating or serpentine ring structure.

In the alternative embodiments of filter members 80, 90, 130, 140 and 150, a plurality of distally extending strut members are provided spaced approximately 120 degrees apart from one and other about the circumference of the filter members, and the distally extending strut members bifurcating once or twice distally in a generally Y-shaped manner as in filter members 80, 130, 140 or 150, or the proximally extending strut members bifurcating proximally in a generally Y-shaped manner and interconnecting with the distally extending generally Y-shaped strut members to form a diamond-like pattern as in filter member 90. In filter members 90 and 140, the circumferential member is formed by the diamond-like pattern formed by the intersection of the plurality of struts. In contrast, in filter members 80, 130 and 150, the circumferential member is formed by at least one undulating or serpentine ring structure which is diametrically expansible. As illustrated in filter members 110, 120 and 130, apical portions of each undulating or serpentine ring structure is interconnected by an interconnecting member 114, 124, 134, respectively, either with an adjacent ring structure, as in filter member 110 or to a distal end 20 of the filter member itself. A longitudinally serpentine section 132 in filter 32 may be provided in conjunction with the interconnecting member 134, to afford greater expansive properties to the circumferential member 137.

According to some embodiments particularly well-suited for placement by femoral or other infrarenal approach, the filter member 16 is characterized by a generally conical filter member 16 having a greater open surface area exposed to the flow of embolic material into the filter at its proximal end, while the distal end has smaller open surface area exposed to the flow of embolic material to capture the embolic material in the distal end of the filter member.

In other embodiments particularly well-suited for placement by a jugular or suprarenal approach, the filter member 16 is characterized by a generally conical filter member 16 having a greater open surface area exposed to the flow of embolic material into the filter at its distal end, which the proximal end of the filter member 16 has a smaller open surface area exposed to the flow to capture smaller embolic material in the distal end of the filter member 16.

Additionally, in all of the embodiments the filter member 16 is self-centering to provide proper apposition against the vascular walls and centering within the lumen of a blood vessel. This maximizes the flow dynamics of the filter member 16 within the blood vessel for purposes of capturing embolic material within the struts of the filter and centers the catheter body member 12 within the vascular lumen.

As noted above, the proximal 32 and distal 34 ports serve as means for measuring flow rates or pressure differentials across the filter 16. This may be accomplished by including flow sensors and/or pressure transducers 19 in operable association with each port 32, 34, with the associated electrical connections to the flow sensors an/or pressure transducers 19 passing through the respective lumens associated with each port 32, 34 and terminating at the proximal end of the catheter body 12. Where flow sensors 19 are employed, a single flow sensor associated with proximal port 32, the distal port 34 or the distal end of outer sheath 22 may be sufficient to detect fluid flow rate at the position of the catheter body 12. By providing a flow sensor at the distal end of sheath 22, the clinician will be able to determine flow velocity at the distal end of the outer sheath 22 prior to introducing the catheter body 12 and make fine adjustments to the placement of the distal end of the outer sheath 22 to ensure proper placement for the filter member 16. Plural flow sensors 19 may be employed and operably associated with each of proximal port 32 and distal port 34 to sense changes in flow velocity across the filter member 16. Alternatively, the flow sensors and/or pressure transducers 19 may reside in communication with the lumens respectively associated with each port 32, 34 at the proximal end of the catheter body 12, thereby eliminating the need for electrical connectors resident with the associated lumens. Furthermore, wireless flow sensors and/or pressure transducers may be provided in communication with each port 32, 34, and be operably coupled to a power source and a transmitter to wirelessly transmit telemetry data from the transducers to a wireless receiver in communication with the transmitter, as is known in the art.

Alternatively, the proximal 32 and distal ports 34 may be used for monitoring or sensing other conditions in the body that are detectable in the blood. For example, analyte sensors may be introduced to either the lumens communicating with the proximal 32 or distal ports 34 or to the ports themselves to monitor and/or sense chemical or biochemical conditions in the body. An example of this application is monitoring or sampling blood glucose levels for diabetes control. Further, the proximal 32 and distal ports 34 may be used for fluid infusion or for withdrawal or evacuation of fluids or other material through the catheter body 12. In this later instance, where the proximal port 32 is positioned to underlay the filter member 16, thrombus collected in the filter member 16 may capable of being lysed, either by thrombolysis through the infusion ports 36 or under the influence of thermal or mechanical lysis, such as by introducing a laser, ultrasound or other system capable of lysing thrombus, which may be introduced through the lumen communicating with the proximal port 32, or the distal port 32 or the guidewire lumen 30, or introduced separately from the CVAF 10, positioned within the space bounded by the filter member 16, lysing thrombus collected in the filter member 16 and evacuating the lysed thrombus through the proximal port 32

It is known that flow rate increases proximally within the venous system. For example a flow rate of 1 L/min is typical in one femoral vein, increases to 2 L/min in the inferior vena cava and increasing another 0.7 to 1 L/min proximate the renal veins. Knowing the typical flow velocities in vessels of different transverse cross-sectional areas, coupled with a flow sensor 19 associated with the multi-lumen catheter body 12 may serve to supplement or replace the requirements for fluoroscopy or sonography in placement of the CVAF 10, 50.

Other sensors, such as, for example, chemosensors, color sensors, electrical sensors or biosensors, may be employed in lieu of or in addition to pressure transducer and/or a flow sensor 19 in order to detect other changes or conditions within the patient's vasculature. For example, color sensors exist that sense color changes in thrombus, such color changes may be displayed and interpreted by the medical practitioner as an indication of thrombus staging. Analyte sensors, such a as a glucose sensor or an oxygen saturation sensor may also be employed.

The filter member 16, or its alternative embodiments described above, may be fixed to the catheter body 12 or may be removably coupled to the catheter body 12 for deployment as either a permanent filter or as a temporary and retrievable vena cava filter. Removable coupling of the filter member to the catheter body 12 may be accomplished with a variety of release and retrieval mechanisms operably associated the catheter body 12 and proximate the diametric transition 15. Non-limiting examples of such release and retrieval mechanisms include a wire release that engages with a the first end 18 of the filter, a cooperating indexed detent and projection interaction between the catheter body 12 and the first end 18 of the filter, such as a detent in the proximal end of the filter and a cooperating projection in the multi-lumen catheter that is positionally indexed to the detent and releasable from the detent, or, alternatively, a helical slot or threads may be formed in the proximal end 18 of the filter and indexed and cooperating projection in the multi-lumen catheter than permits engagement and disengagement with the helical slot or threads.

In use, an introducer sheath is first placed into the body in a normal manner for introducing a central venous line, such as by the Seldinger technique. Specifically, after accessing a vein using a large bore needle, under local anesthesia, a guidewire is inserted through the needle bore and passed into the vein. Once the guidewire is positioned, the needle is withdrawn, and a dilator together with the introducer sheath introduced over the guidewire. Once the introducer sheath is positioned at a desired location within the venous system under radiography, the dilator may be removed from the patient. Radiopaque markers associated with the introducer sheath may be employed to assist in positional visualization of the distal end of the introducer sheath. The outer sheath 22 covering the filter 16 is removed while introducing the filter member 16 and catheter body 12 into the introducer sheath. The outer sheath 22 constrains the filter member 16 during its passage through the introducer sheath and positioning the distal end of the catheter within the patient's vasculature. Once the distal end of the catheter body 12 reaches the distal end of the introducer sheath, the filter is deployed. If the filter therapy alone is desired, the filter member 16 is detached from the catheter body 12 and the catheter body 12, introducer sheath and guidewire is withdrawn from the patient. Where both central venous access and filter therapy is desired, the introducer sheath and catheter body 12 with the filter member 16 is left in the patient until withdrawal is required.

Retrieval and removal of a detached filter member 16 is accomplished using a second procedure under local anesthesia which substantially replicates the placement of the CVAF, with a capture sheath (not shown), similar to introducer sheath, being introduced, a retrieval catheter being introduced through the sheath, and engaging the filter member 16, then withdrawn into the capture sheath to collapse the filter member 16, with the entire assembly of the filter member 16, catheter body 12, outer sheath 22 and guidewire, if used, is withdrawn from the patient.

As depicted in FIGS. 16A and 16B, which depict the undeployed state (FIG. 16A) and the deployed state (FIG. 16B) of the filter member 216, respectively, common to each of the embodiments of the present invention 200 is an inner catheter 214 that carries the vena cava filter 216 at a distal end thereof. The inner catheter 214 is concentrically and reciprocally engaged within an outer sheath 222 such that relative axial movement of the inner catheter 214 and the outer sheath 222 either exposes the vena cava filter 216 for deployment or captures the vena cava filter 216 for retrieval. A first hub member 225 is coupled to a proximal end of the outer sheath 222 and a second hub member 227 is coupled to a proximal end of the inner catheter 214. First hub member 225 and second hub member 227 are engageable, such as by a threaded, bayonet, snap fit, friction fit or interference fit fitting, to secure the inner catheter 214 within the outer sheath 222 and restrict relative axial movement of the two elements after deployment of the vena cava filter 216. A flush line 229 communicates with the first hub member 225 and is in fluid communication with a luminal space within the outer sheath 222. A plurality of fluid lines 231, 233, 235, 237 communicate with the second hub member 227 and are each in fluid communication with one of the plural lumens within the inner catheter member 214, e.g., lumens communicating with the proximal, distal or infusion ports (not shown). A distal tip 26 is provided at a distal end of the inner catheter.

A jugular approach necessitates that the catheter be introduced retrograde relative to the vector of blood flow within the vena cava, i.e., the catheter is introduced through the jugular vein and directed inferiorly toward an infrarenal position. Additionally, since the blood flow opposes the distal end of the catheter and passes toward the proximal end, the vena cava filter must open inferiorly such that its largest diametric section in apposition to the vessel walls opens toward the distal end of the catheter rather than toward the proximal end of the catheter as with the femoral approach.

Figure 17:
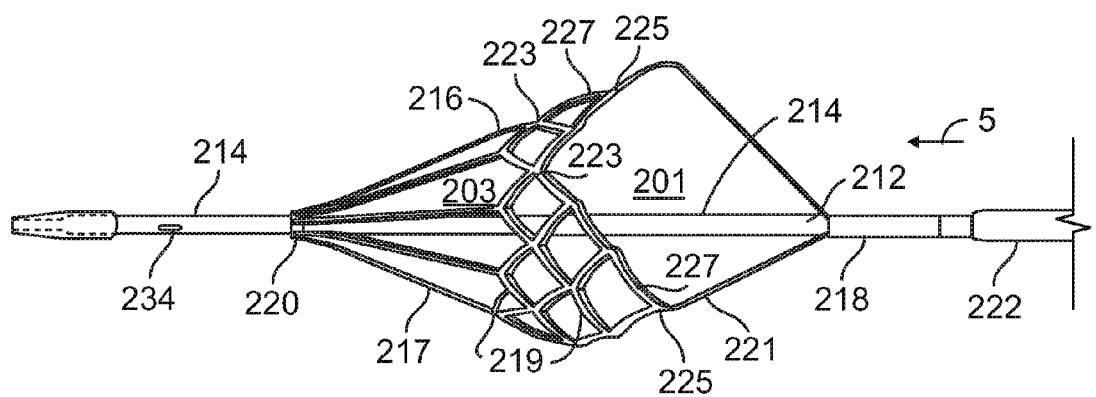
FIG. 17 is a side elevational view of an vena cava filter member in its expanded state in accordance with one embodiment of the present invention.
Figure 18:
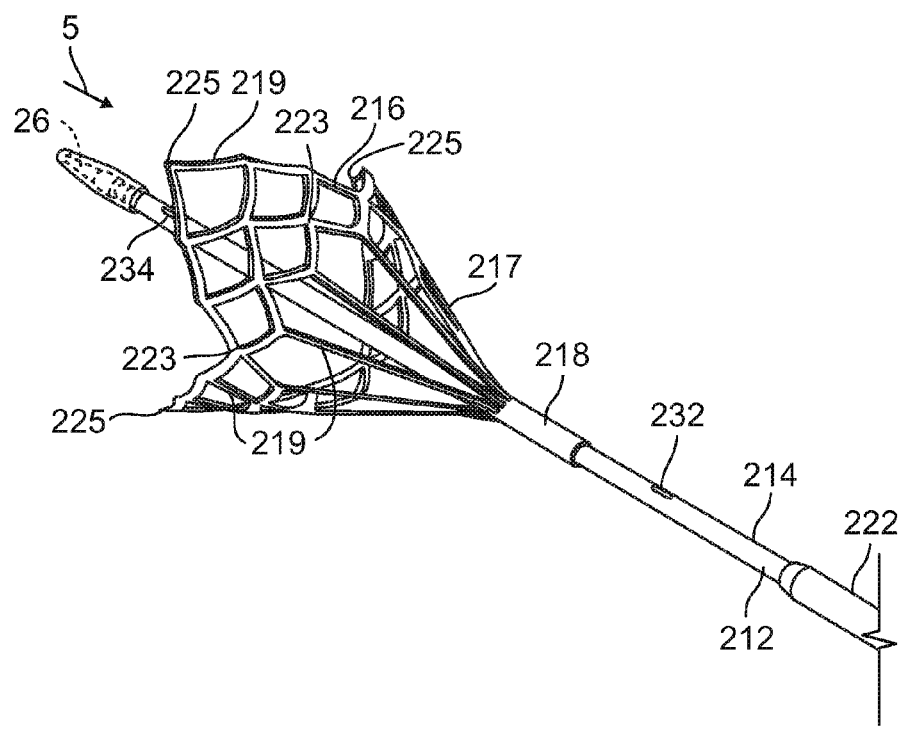
FIG. 18 is a perspective view of a vena cava filter member in its expanded state in accordance with an alternative embodiment of the present invention.
Figure 19:
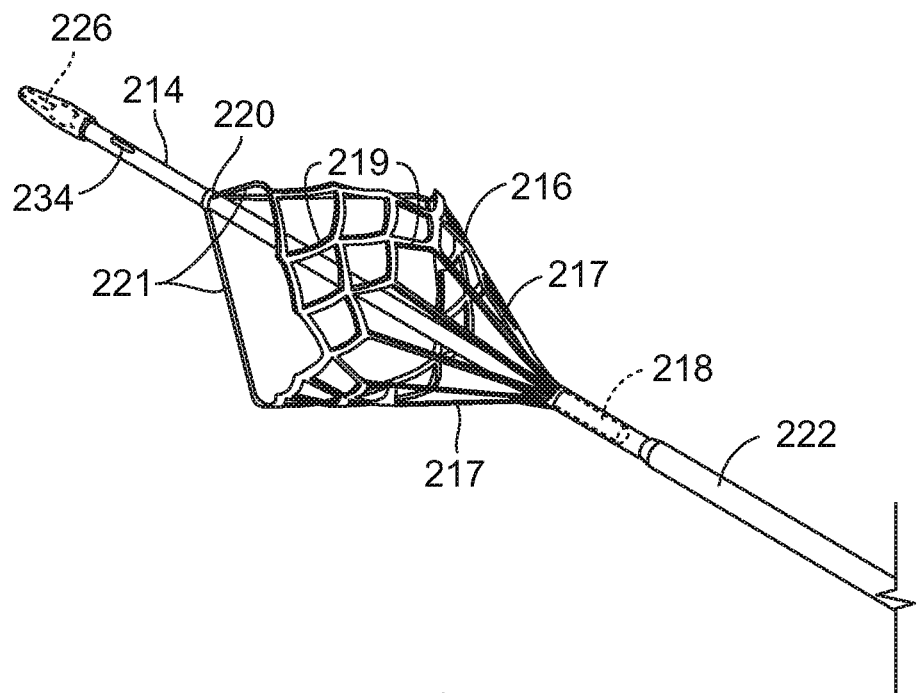
FIG. 19 is a perspective view of a vena cava filter member in its expanded state in accordance with yet another embodiment of the present invention.
Figure 20:
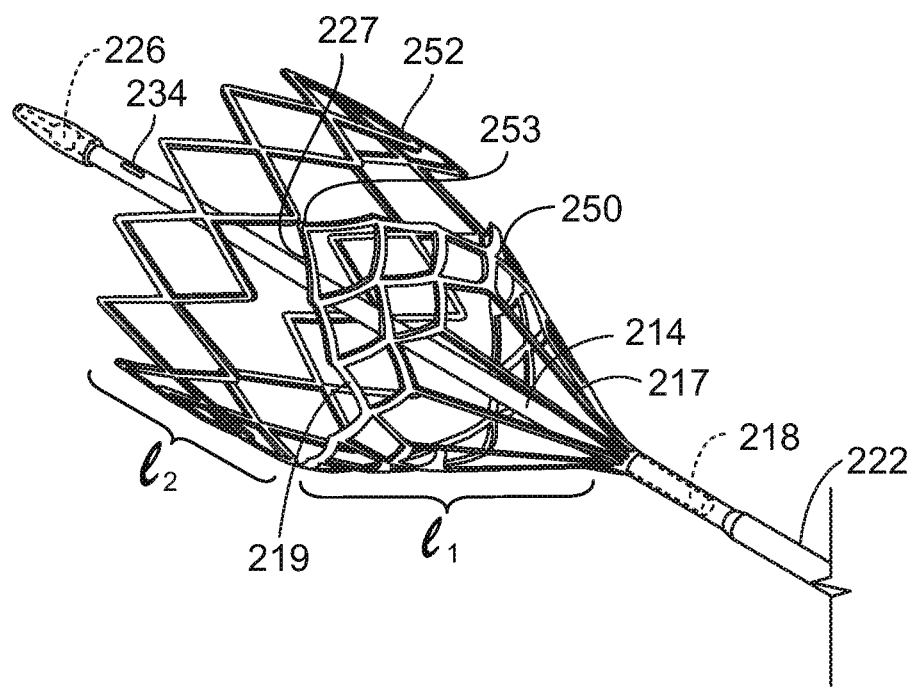
FIG. 20 is a perspective view of a vena cava filter member in its expanded state in accordance with still another embodiment of the present invention

FIGS. 17-20 depict alternative embodiments of vena cava filter members in accordance with the present invention. FIG. 17 illustrates a filter orientation for a femoral approach, while FIGS. 18-20 illustrate a filter orientation for a jugular approach. As illustrated in FIG. 17, filter member 216 defines a relatively larger volume open space 201 and a relatively smaller volume open space 203. Open spaces 201 and 203 are bounded by structural members of the filter member 216 and are both open toward the direction of blood flow indicated by arrow 5, with larger open space 201 being relatively upstream the blood flow relative to smaller open space 203 in both the femoral or the jugular orientation of filter member 216.

As with all previous embodiments described of the filter member, filter member 216 is formed of plural interconnected structural elements. In accordance with the preferred embodiments of the filter members of the present invention, and as particularly exemplified by filter member 216, the filter member has a first end 218 and a second end 220, at least one of which is attached to the distal section 214 of the catheter body 212. First structural members 217 extend generally axially, either proximally as shown in FIG. 17 or distally as shown in FIG. 18, along the longitudinal axis of the filter member 216. Again, it is understood that use of the terms "proximal" or "proximally" and "distal" or "distally" are intended to refer to positions relative to the longitudinal axis of the catheter body 212. The first structural members 217 are connected to either the first end 218 or the second end 220 of the filter member 216. Second structural members 219 are connected to the first structural members 217 at an end of the first structural members 217 which is opposite that connected to either the first end 218 or the second end 220 of the filter member 216. In accordance with a preferred embodiment of the invention, the second structural members 219 form at least two successive zigzag shaped structures which are connected to an end of the first structural members and at opposing apices 223 to form conjoined ring-like structures about the circumference of the filter member 216. In this manner the second structural members 219 generally define lattice-like pattern upon diametric expansion of the filter member 216. The lattice-like pattern formed by the second structural members 219 projects axially along the longitudinal axis of the catheter 214 tapering to form at least one petal-like projection 225 that terminates in an terminal apex member 227. As will be appreciated by those skilled in the art, FIG. 17 depicts three petal like projections 225, with one being behind the plane of the figure and, therefore, not shown. Each of the petal-like projections 225 act to engage and oppose vascular wall surfaces to seat the filter member 216 against the vessel wall, and center the filter member and catheter 214 within the vascular lumen. As illustrated in FIG. 17, third structural members 221 are provided and are connected to each of the terminal apex members 227 and extend axially relative to the catheter 214 and connect with a second end 218 of the filter member 216.

In the embodiment illustrated in FIG. 17, which is an orientation of the filter member 216 for a femoral approach, and in the embodiment illustrated in FIG. 19, which is an orientation of the filter member 216 for a jugular approach, the first end 218 of the filter member 216 is fixedly connected to the catheter 212, while the second end 220 of the filter member 216 is movably coupled to the catheter 212 and moves axially along the catheter 216 upon expansion or contraction of the filter member 216.

FIG. 18 depicts an embodiment of the filter member 216 identical to that illustrated in FIG. 19, with the sole exception that the third structural members 219 and the second end 220 of the filter member 216 are omitted. In this embodiment, the terminal apex member 227 of each petal-like member 225 are not connected to a second end 220 of the filter member 216 by the third structural members 219.

FIG. 20 depicts an alternative embodiment of the filter member 216 which is similar to that depicted in FIG. 18, except that at least one circumferential ring member 252 is connected to the terminal apex member 227 of each of the petal-like members 225 at a juncture 253 with the terminal apex member 227. The addition of the additional circumferential ring member 252 results in a relative elongation over the length L1 of the filter member 216 depicted in FIG. 18 by a length L2 which facilitates additional apposition between the filter member 216 and the vascular wall and stabilization of the petal-like members 225.

Figure 21A:
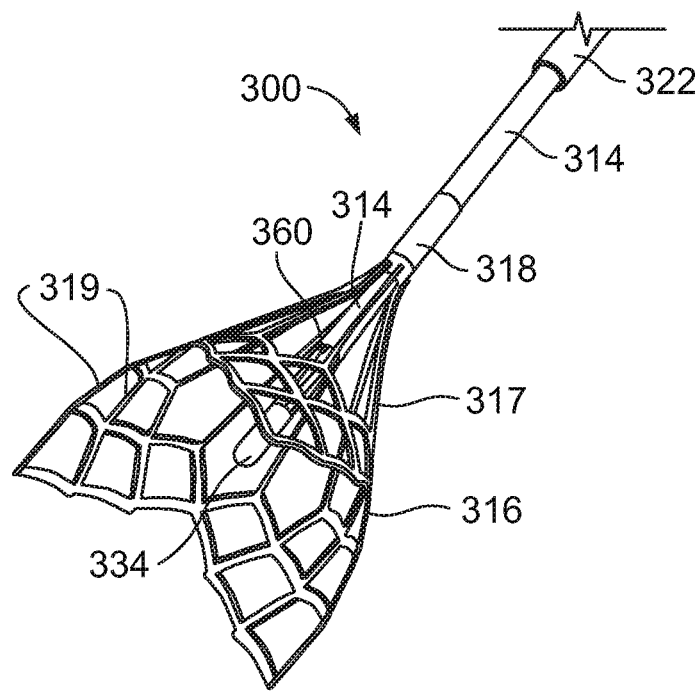
FIGS. 21A and 21B are perspective views of a vena cava filter member mounted at a distal end of a central line catheter having a distal balloon.
Figure 21B:
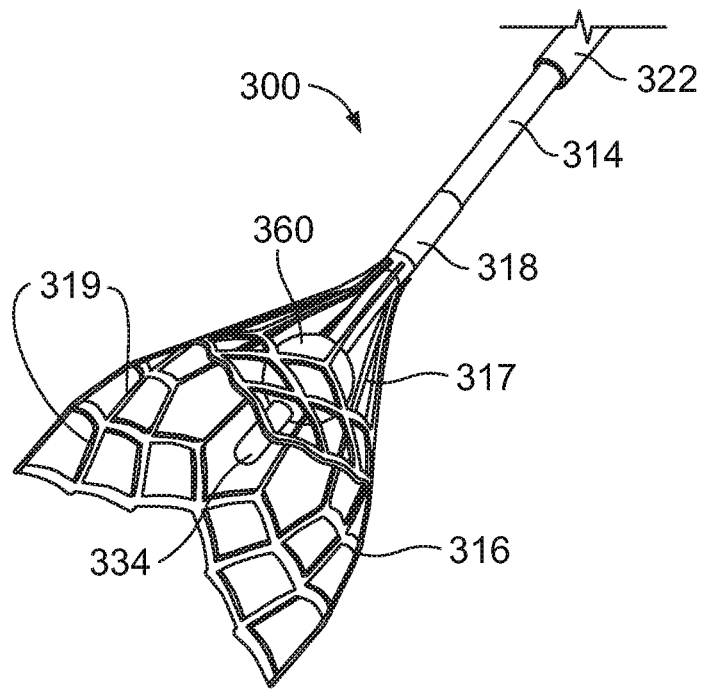

FIGS. 21A and 21B depict an alternative embodiment of the filter member 216 in FIG. 18, having first end 318, first structural elements 317 and second structural elements 319 all analogously arranged as in the embodiment of FIG. 18. Filter member 300, however, employs a modified distal end 314 of the catheter 312 to include an expansive balloon 360. The guidewire lumen of the multi-lumen catheter 312 may be used in place of a distal port for either condition sensing, flushing, infusion or the like. The expansive balloon 360 may be used to break up thrombus captured within the filter member 316, either by mechanical force through serial dilatation or by infusion of a thrombolytic agent through openings in the balloon 360. FIG. 21A depicts the balloon 360 in its collapsed state, whereas FIG. 21B depicts the balloon in its expanded state.

Alternatively, an expansive balloon 360 may be placed proximal the filter member 300 and serve to temporarily occlude the vessel to facilitate aspiration or evacuation of thrombus from the filter member 30.

Figure 22A:
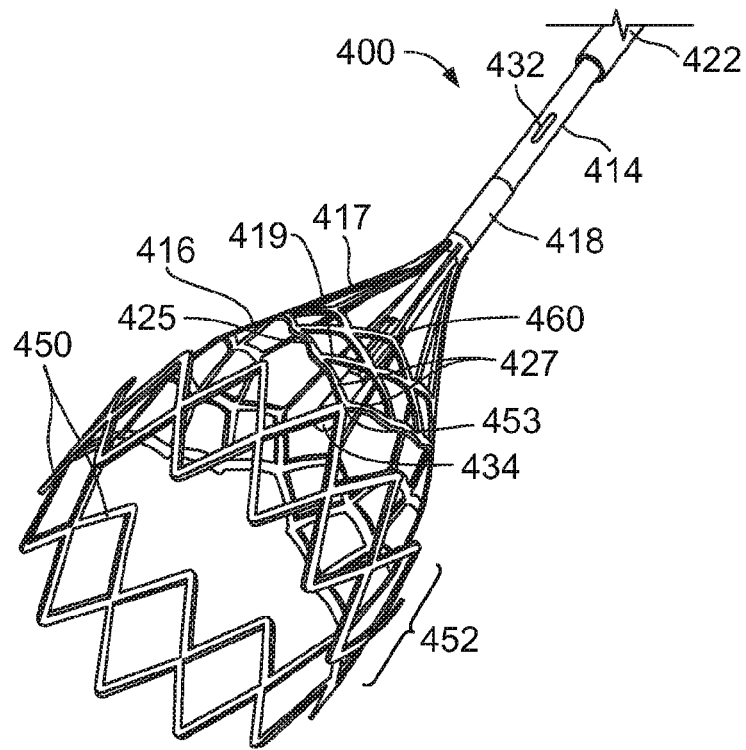
FIGS. 22A and 22B are perspective views of an alternative embodiment of a vena cava filter member mounted at a distal end of a central line catheter having a distal balloon.
Figure 22B:
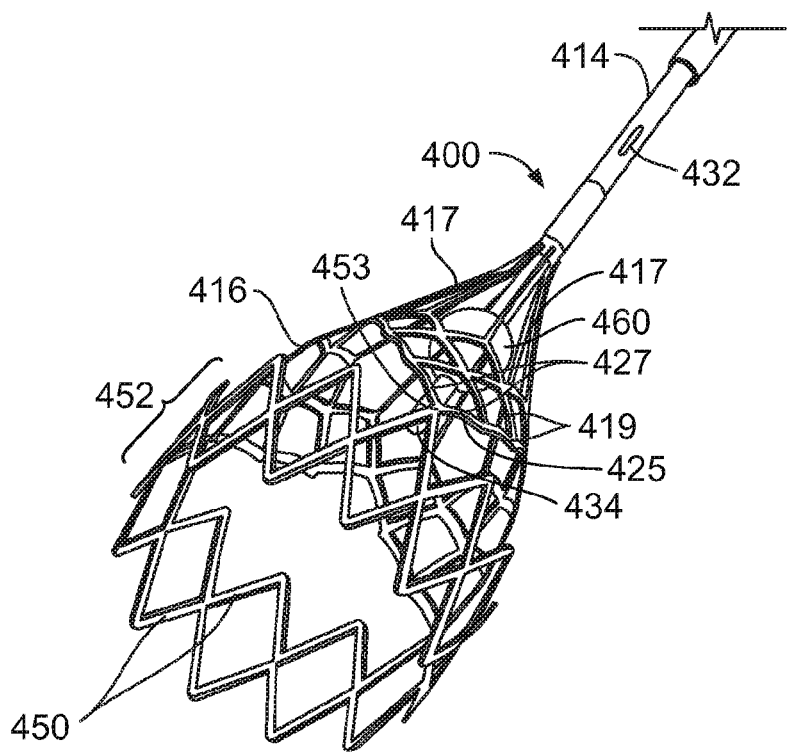

Finally, FIGS. 22A and 22B depict an alternative embodiment of the filter member 216 in FIG. 20 having first end 418, first structural elements 417 and second structural elements 419, at least one circumferential ring member 452 connected to the terminal apex member 427 of each of the petal-like members 425 at a juncture 453 with the terminal apex member 427; all analogously arranged as in the embodiment of FIG. 20. Filter member 400, however, employs a modified distal end 414 of the catheter 412 to include an expansive balloon 460. The guidewire lumen of the multi-lumen catheter 412 may be used in place of a distal port for either condition sensing, flushing, infusion or the like. The expansive balloon 460 may be used to break up thrombus captured within the filter member 416, either by mechanical force through serial dilatation or by infusion of a thrombolytic agent through openings in the balloon 460. FIG. 22A depicts the balloon 460 in its collapsed state, whereas FIG. 22B depicts the balloon in its expanded state.

Again, an expansive balloon 460 may be positioned proximal the filter member 416 to permit temporary occlusion of the blood vessel and permit aspiration or evacuation of thrombus from the filter member 416.

It will be appreciated by those skilled in the art that in all embodiments of the described central venous access filter, the filter member has a relatively larger opening that is open inferiorly in a direction that opposes the blood flow vector and employs structural elements that taper superiorly along the direction of the blood flow vector to reduce the open surface area of the filter member and capture thrombus.

Thus there has been described a central venous access filter in accordance with the foregoing embodiments of the invention which include, generally, a multi-lumen catheter body, a filter member and an introducer sheath. The multi-lumen catheter body has a plurality of ports each of which are in fluid flow communication with at least one lumen in the multi-lumen catheter body. Lumens may include a central guidewire lumen useful for tracking over a guidewire and/or larger volume infusion of bioactive agents, intravenous fluids, blood transfusions, or other fluids; infusion lumens in communication with infusion ports positioned to direct fluids to the space bounded by the filter member for introducing bioactive agents, including thrombolytic agents or flushing agents, including pressurized fluids for mechanical thrombolysis directly to the capture site of the thrombus in the filter member; and lumens communicating with proximal and distal ports which may also be used for fluid introduction and/or may house or communicate with sensors, such as pressure transducers, flow sensors, analyte sensors, color sensors, optical sensors or the like. The filter member may be detachable from the multi-lumen catheter body to permit temporary filter placement and later retrieval by a detachment mechanism that cooperates between the filter and the multi-lumen catheter body. These and other aspects of the present invention are provided by way of non-limiting examples, with the claims appended hereto serving to define the scope of the subject matter regarded as the invention.

What is claimed is:

1. A method of capturing thrombus within a blood vessel, comprising the steps of:

introducing a multi-lumen catheter having a filter member coupled thereto, wherein the filter member is circumferentially coupled about a distal region of the multi-lumen catheter and has a first end coupled circumferentially in fixed relation to the multi-lumen catheter and a second end circumferentially moveably coupled to the multi-lumen catheter, the filter member consisting of:

a plurality of struts configured to form a generally frustroconical proximal section of the filter member tapering proximally and having proximal interstitial openings, and a generally frustroconical distal section of the filter member tapering distally and having distal interstitial openings, the frustroconical proximal section having a length that is greater than or less than a length of the frustroconical distal section, each of the proximal interstitial openings having an open surface area either greater than or less than the open surface area of each of the distal interstitial openings;

where the filter member is configured to expand in a patient's blood vessel such that a transverse dimension of the filter decreases in the direction of the patient's blood flow to collect thrombi, wherein the vena cava filter member centers the multi-lumen catheter within a blood vessel lumen;

deploying the multi-lumen catheter within a blood vessel such that the filter member expands so that the larger interstitial openings between the frustroconical distal or proximal sections open facing a patient's blood flow;

inserting an ultrasound imaging system operable to detect a condition of the filter member into a lumen of the multi-lumen catheter and positioning the ultrasound imaging system in a region of the multi-lumen catheter bounded by the filter member; and imaging the filter member with the ultrasound imaging system, wherein the condition of the filter member is the presence of a thrombus in the filter member.

2. The method according to claim 1, wherein the step of imaging the filter member further comprises confirming the presence of a thrombus captured within the filter member.

3. The method according to claim 1, wherein the ultrasound imaging system is configured to be deployed by insertion into a lumen of the multi-lumen catheter to permit imaging within a region bounded by the filter member.

4. The method according to claim 3, wherein the step of inserting the imaging system into the lumen of the multi-lumen catheter further comprises disposing an imaging tip in a region of the multi-lumen catheter bounded by the filter member.

5. The method according to claim 1, wherein the step of imaging the filter member further comprises imaging the filter member from within the multi-lumen catheter; and infusing a fluid through at least one lumen in the multi-lumen catheter in communication with at least one infusion port passing through a sidewall of the multi-lumen catheter and open to an inner spatial area bounded by the filter member.

6. A multi-lumen vena cava filter catheter, comprising:
a catheter body having a first lumen and a second lumen, the first lumen and the second lumen being separated by a portion of the catheter body, the catheter body also having a first distal opening in communication with the first lumen and a second distal opening in communication with the second lumen, wherein the first distal opening is disposed a first distance proximally from a distal end of the catheter body and the second distal opening is disposed a second distance proximally from the distal end of the catheter body;
a vena cava filter member circumferentially coupled about a distal end of the central venous line catheter body and having a first end coupled circumferentially in fixed relation to the central venous line catheter body and a second end circumferentially moveably coupled to the central venous line catheter body, the vena cava filter member consisting of a plurality of struts configured to form a generally frustroconical proximal section of the vena cava filter member tapering proximally and having proximal interstitial openings, and a generally frustroconical distal section of the vena cava filter member tapering distally and having distal interstitial openings, the frustroconical proximal section having a length that is greater than or less than a length of the frustroconical distal section, each of the proximal interstitial openings having an open surface area either greater than or less than the open surface area of each of the distal interstitial openings; the vena cava filter member being positioned generally intermediate the first distal opening and second distal opening and configured to be expanded in a patient's blood vessel such that a transverse dimension of the filter decreases in the direction of the patient's blood flow to collect thrombi, wherein the vena cava filter member centers the central venous line catheter body within a blood vessel lumen; and
an ultrasound imaging system operable to detect a condition of the filter, wherein the condition of the filter member is the presence of a thrombus in the filter member.

7. The medical device according to claim 6, wherein ultrasound imaging system is configured to be deployed by insertion into a lumen of the multi-lumen catheter to permit imaging within a region bounded by the filter member.

8. The medical device according to claim 7, wherein the imaging system is configured to image the filter member in situ.

9. The medical device according to claim 6, wherein the imaging system further comprises an imaging core, a drive cable, and an imaging tip.

10. The medical device according to claim 9, wherein the imaging tip is adapted to be positioned within the multi-lumen catheter body in a region bounded by the filter member.

11. A multi-lumen vena cava filter catheter, comprising:
a catheter body having a first lumen and a second lumen, the first lumen and the second lumen being separated by a portion of the catheter body, the catheter body also having a first distal opening in communication with the first lumen and a second distal opening in communication with the second lumen, wherein the first distal opening is disposed a first distance proximally from a distal end of the catheter body and the second distal opening is disposed a second distance proximally from the distal end of the catheter body;
a vena cava filter member circumferentially coupled about a distal end of the central venous line catheter body and having a first end coupled circumferentially in fixed relation to the central venous line catheter body and a second end circumferentially moveably coupled to the central venous line catheter body, the vena cava filter member consisting of a plurality of struts configured to form a generally frustroconical proximal section of the vena cava filter member tapering proximally and having proximal interstitial openings, and a generally frustroconical distal section of the vena cava filter member tapering distally and having distal interstitial openings, the frustroconical proximal section having a length that is greater than or less than a length of the frustroconical distal section, each of the proximal interstitial openings having an open surface area either greater than or less than the open surface area of each of the distal interstitial openings; the vena cava filter member being positioned generally intermediate the first distal opening and second distal opening and configured to be expanded in a patient's blood vessel such that a transverse dimension of the filter decreases in the direction of the patient's blood flow to collect thrombi, wherein the vena cava filter member centers the central venous line catheter body within a blood vessel lumen; and
a sheath having an outer wall surface and an inner wall surface, the sheath configured to be movably disposed over the catheter body and the vena cava filter member such that the sheath is longitudinally displaceable relative to the catheter body to deploy the vena cava filter member; and
an ultrasound imaging system operable to detect a condition of the filter, wherein the condition of the filter member is the presence of a thrombus in the filter member.

12. The medical device according to claim 11, wherein the ultrasound imaging system is configured to be deployed by insertion into a lumen of the multi-lumen catheter to permit imaging within a region bounded by the filter member.

13. The medical device according to claim 12, wherein the imaging system is configured to image the filter member in situ.

14. The medical device according to claim 11, wherein the imaging system further comprises an imaging core, a drive cable, and an imaging tip.

15. The medical device according to claim 14, wherein the imaging tip is adapted to be positioned within the multi-lumen catheter body in the region bounded by the filter member.

* * * * *